(12) United States Patent
Narhi et al.

(10) Patent No.: US 6,743,422 B1
(45) Date of Patent: Jun. 1, 2004

(54) KERATINOCYTE GROWTH FACTOR-2 PRODUCTS

(75) Inventors: Linda Owers Narhi, Camarillo, CA (US); Timothy David Osslund, Camarillo, CA (US)

(73) Assignee: Amgen, Inc., Thousand Oaks, CA (US)

(*) Notice: Subject to any disclaimer, the term of this patent is extended or adjusted under 35 U.S.C. 154(b) by 0 days.

(21) Appl. No.: 09/284,100

(22) PCT Filed: Oct. 15, 1997

(86) PCT No.: PCT/US97/18607

§ 371 (c)(1),
(2), (4) Date: Apr. 7, 1999

(87) PCT Pub. No.: WO98/16642

PCT Pub. Date: Apr. 23, 1998

Related U.S. Application Data

(60) Provisional application No. 60/033,046, filed on Dec. 10, 1996, provisional application No. 60/032,781, filed on Dec. 6, 1996, and provisional application No. 60/028,493, filed on Oct. 15, 1996.

(51) Int. Cl.$^7$ .................. C07K 14/475; C12N 1/21; C12N 5/16; C12N 15/19; C12N 15/63

(52) U.S. Cl. ................ 424/85.1; 514/2; 514/8; 514/12; 435/320.1; 435/252.3; 435/254.11; 435/325; 435/69.1; 435/69.4; 530/351; 530/350; 536/23.5; 536/23.1

(58) Field of Search .................. 530/399, 350, 530/351; 435/69.4, 71.1, 71.2, 325, 352.3, 254.11, 320.1, 69.1; 536/23.5, 23.51; 574/2, 5, 12; 424/85.1

(56) References Cited

U.S. PATENT DOCUMENTS

| | | |
|---|---|---|
| 3,917,824 A | 11/1975 | Camble et al. |
| 4,820,690 A | 4/1989 | Gregory et al. |
| 4,959,314 A | 9/1990 | Mark et al. |
| 5,194,596 A | 3/1993 | Tisher et al. |
| 5,302,702 A | 4/1994 | Seddon et al. |
| 5,310,883 A | 5/1994 | Seddon et al. |
| 5,350,836 A | 9/1994 | Kopchick et al. |
| 5,491,220 A | 2/1996 | Seddon et al. |
| 5,578,566 A | 11/1996 | Bottaro et al. |
| 5,589,451 A | 12/1996 | Wilson |
| 5,654,405 A | 8/1997 | Rubin et al. |
| 5,665,870 A | 9/1997 | Rubin et al. |
| 5,677,278 A | 10/1997 | Gospodarowicz et al. |
| 5,707,805 A | 1/1998 | Rubin et al. |
| 5,773,586 A | 6/1998 | Gospodarowicz et al. |
| 5,814,605 A | 9/1998 | Pierce et al. |
| 5,824,643 A | 10/1998 | Pierce et al. |
| 5,843,883 A | 12/1998 | Gospodarowicz et al. |
| 5,863,767 A | 1/1999 | Gospodarowicz et al. |
| 6,077,692 A | 6/2000 | Ruben et al. |
| 6,238,888 B1 | 5/2001 | Gentz et al. |

FOREIGN PATENT DOCUMENTS

| | | |
|---|---|---|
| EP | 0 241 136 A2 | 10/1987 |
| EP | 0 298 723 A1 | 1/1989 |
| EP | 0 319 052 A3 | 6/1989 |
| EP | 0 319 052 A2 | 6/1989 |
| EP | 0 455 422 A2 | 11/1991 |
| EP | 0 486 861 A1 | 5/1992 |
| EP | 0 510 662 A1 | 10/1992 |
| EP | 0619 370 A1 | 10/1994 |
| JP | 6345666 | 12/1994 |
| WO | WO 90/08771 | 8/1990 |
| WO | WO 90/12874 A2 | 11/1990 |
| WO | WO 92/11360 A1 | 7/1992 |
| WO | WO 92/14480 A1 | 9/1992 |
| WO | WO 92/22304 A1 | 12/1992 |
| WO | WO 93/21908 A1 | 11/1993 |
| WO | WO 94/22427 A1 | 10/1994 |
| WO | WO 94/23032 A1 | 10/1994 |
| WO | WO 94/25057 A1 | 11/1994 |
| WO | WO 95/01434 A1 | 1/1995 |
| WO | WO 95/03831 A1 | 2/1995 |
| WO | WO 95/08630 A1 | 3/1995 |
| WO | WO 95/21258 A1 | 8/1995 |
| WO | WO 95/24928 A2 | 9/1995 |
| WO | WO 96/11949 A2 | 4/1996 |
| WO | WO 96/11950 A1 | 4/1996 |
| WO | WO 96/11951 A2 | 4/1996 |
| WO | WO 96/11951 A3 | 4/1996 |
| WO | WO 96/11952 A1 | 4/1996 |
| WO | WO 96/22369 A1 | 7/1996 |
| WO | WO 96/25422 A1 | 8/1996 |
| WO | WO 97/13857 A1 | 4/1997 |
| WO | WO 97/20929 A1 | 6/1997 |
| WO | WO 98/06844 A1 | 2/1998 |
| WO | WO 98/16243 A1 | 4/1998 |
| WO | WO 98/24813 A2 | 6/1998 |

OTHER PUBLICATIONS

McGwire et al. 1996, Posttranslational regulation of a leishmania HEXXH metalloprotease (gp63). vol. 271, pp. 7903–7909.*

Abraham et al., "Human Basic Fibroblast Growth Factor: Nucleotide Sequence and Genomic Organization", The EMBO Journal, 5(10):2523–2528 (1986).

Ago et al., "Crystal Structure of Basic Fibroblast Growth Factor at 1.6 Å Resolution", J. Biochem., 110:360–363 (1991).

Alarid et al., "Keratinocyte Growth Factor Functions in Epithelial Induction During Seminal Vesicle Development", Proc. Natl. Acad. Sci. USA, 91:1074–1078 (1994).

(List continued on next page.)

Primary Examiner—Elizabeth Kemmerer
(74) Attorney, Agent, or Firm—McDonnell Boehnen Hulbert & Berghoff

(57) ABSTRACT

The present invention concerns variants and chemical derivates of keratinocyte growth factor-2 (KGF-2) protein. Also disclosed are nucleic acid molecules encoding such variants, as well as methods for using such variants and chemical derivates to stimulate epithelial cell proliferation.

21 Claims, 8 Drawing Sheets

OTHER PUBLICATIONS

Arakawa et al., "Production and Characterization of an Analog of Acidic Growth Factor with Enhanced Stability and Biological Activity", Protein Engineering, 6(5):541–546 (1993).

Bare et al., "Effect of Cysteine Substitutions on the Mitogenic Activity and Stability of Recombinant Human Keratinocyte Growth Factor", Biochemical and Biophysical Research Communications, 205(1):872–879 (1994).

Bottaro et al., "Characterization of the Receptor for Keratinocyte Growth Factor", The Journal of Biological Chemistry, 265(22):12767–12770. (1990).

Burgess et al., "Structural Evidence That Endothelial Cell Growth Factor Beta is the Precursor of Both Endothelial Cell Growth Factor Alpha and Acidic Fibroblast Growth Factor", Proc. Natl. Acad. Sci., 83:7216–7220 (1986).

Burgess and Maclag, "The Heparin–binding (Fibroblast) Growth Factor Family of Proteins", Annu. Rev. Biochem., 58:575–606 (1989).

Canatan et al., "Expression of Keratinocyte Growth Factor (KGF) on Normal and Archival Canine Hyperplastic Prostatic Tissues", FASEB Journal, 8(4–5):A930, Abstract 5388 (1994).

Chedid et al., "Regulation of Keratinocyte Growth Factor Gene Expression by Interleukin 1", The Journal of Biological Chemistry, 269(14):10753–10757 (1994).

Chen et al., "Aggregation Pathway of Recombinant Human Keratinocyte Growth Factor and Its Stabilization", Pharmaceutical Research, 11(11):1581–1587 (1994).

Chlu & O'Keefe, "Placental Keratinocyte Growth Factor: Partial Purification and Comparison with Epidermal Growth Factor", Archives of Biochemistry and Biophysics, 269(1): 75–85 (1969).

Cleland et al., "The Development of Stable Protein Formulations: A Close Look at Protein Aggregation, Deamidation, and Oxidation", Critical Reviews in Therapeutic Drug Carrier Systems, 10(4):307–377 (1993).

Coulier et al., "Of Worms and Men: An Evolutionary Perspective on the Fibroblast Growth Factor (FGF) and FGF Receptor Families", Journal of Molecular Evolution, 44:43–56 (1997).

Dabora et al., "Effect of Polyanions on the Refolding of Human Acidic Fibroblast Growth Factor", The Journal of Biological Chemistry, 266(35):23637–23640 (1991).

Dekowski et al., "Dexamethasone Inhibits Keratinocyte Growth Factor (KGF) mRNA Expression in Human Fetal Lung Explants", Pediatric Research, 35(4 Part 2):65A, Abstract 378 (1994).

Delli–Bovi et al., "An Oncogene Isolated by Transfection of Kaposi's Sarcoma DNA Encodes a Growth Factor That is a Member of the FGF Family", Cell, 50:729–737 (1987).

Dickson & Peters, "Potential Oncogene Product Related to Growth Factors", Nature, 326:833 (1987).

Dignass et al., "Fibroblast Growth Factors Modulate Intestinal Epithelial Cell Growth and Migration", Gastroenterology, 106(4):A603 (1994).

Diugosz et al., "KGF Induces TGFa Expression and Activates the EGF Receptor Signaling Pathway to Alter Keratinocyte Growth and Differentiation In Vitro", Journal of Investigative Dermatology, 102(4):527, Abstract 24 (1994).

Diugosz et al., "KGF Induces TGFa Expression and Activates the EGF Receptor to Alter Keratinocyte Growth and Differentiation in Vitro", Proceedings of the American Association of Cancer Research Annual Meeting, 35(0):37, Abstract 221 (1994).

Emoto et al., "Structure and Expression of Human Fibroblast Growth Factor–10*", J. Biol. Chem., 272(37):23191–23194 (1997).

Eriksson et al., "Refinement of the Structure of Human Basic Fibroblast Growth Factor at 1.6A Resolution and Analysis of Presumed Heparin Binding Sites by Selenate Substitution", Protein Science, 2:1275–1284 (1993).

Finch et al., "Human KGF is FGF–Related with Properties of a Paracrine Effector of Epithelial Cell Growth", Science 245:752–755 (1989).

Fusenig et al., "Paracrine Regulation of Keratinocyte Growth and Differentiation by Epithelial–Mesenchymal Interactions", Supplement 0(18C):273, Abstract PZ022 (1994).

Gimenez–Gallego et al., "Brain–derived Acidic Fibroblast Growth Factor: Complete Amino Acid Sequence and Homologies", Science, 230:1385–1388 (1986).

Gimenez–Gallego, et al., "Fibroblast Growth Factors, Proteins with a Broad Spectrum of Biological Activities", Neurological Research, 16:313–316 (1994).

Guo et al., "Epidermal Expression of KGF Causes Remarkable Changes in the Skin of Transgenic Mice", Journal of Cellular Biochemistry, Abstract Supplement 17A, Abstract BZ642:317 (1993).

Habazzetti et al., Structure of Hisactophilin is Similar to Interleukin–1 and Fibroblast Growth Factor, Nature, 359:855–858 (1992).

Havill et al., "Keratinocyte Growth Factor (rhKGF) Has Hepatic Stimulatory Effects in Vivo", FASEB Journal, 8(4–5)A930, Abstract 5387 (1994).

Hebda et al., "Keratinocyte Growth Factor: Stimulation of Epidermal Regeneration in Partial Thickness Wounds in Pig Skin", J. Invest. Dermatol., 100(4):557, Abstract 414 (1993).

Imagawa et al., "Keratinocyte Growth Factor and Acidic Fibroblast Growth Factor are Mitogens for Primary Cultures of Mammary Epithelium", Biochem. Biophys. Res. Commun. (USA), 204(3):1165–1169 (1994).

Inatomi et al., "Keratinocyte Growth Factor (KGF) Accelerates Corneal Epithelial Wound Healing in Rabbits", Investigative Ophthalmology & Visual Science, 35(4):1318, Abstract 299 (1994).

Ishii et al., "Preferential Expression of the Third Immunoglobulin–like Domain of K–sam Product Provides Keratinocyte Growth Factor–dependent Growth in Carcinoma Cell Lines", Cancer Research, 54(2):518–522 (1994).

Itoh et al., "Keritinocyte Growth Factor as a Mitogen for Primary Culture of Rat Hepatocytes", Biochem. Biophys. Res. Commun., 192(3):1011–1015 (1993).

Jaye et al., "Human Endothelial Cell Growth Factor: Cloning, Nucleotide Sequence, and Chromosome Localization", Science, 233:541–545 (1986).

Jiminez et al., "Effect of Topical Keratinocyte Growth Factor–2 On Wound Healing in a Glucocorticoid–Impaired Model", Journal of Cutaneous Pathology, 24(2):105 (1997).

Jiminez et al., "Effect of Keratinocyte Growth Factor–2 on Cell Proliferation in Vivo", FASEB Journal, 11(3): A523 (Abstract 3025) (1997).

Kan et al., "Receptor Phenotype Underlies Differential Response of Hepatocytes and Nonparenchymal Cells to Heparin–binding Fibroblast Growth Factor Type 1 (aFGF) and Type 2 (bFGF)", In Vitro Cell Dev Biol, 28A(7–8):515–520 (1992).

Koji et al., "Progesterone–dependent Expression of Keratinocyte Growth Factor mRNA in Stromal Cells of the Primate Endometrium: Keratinocyte Growth Factor as a Progestomedin", The Journal of Cell Biology, 125(2):393–401 (1994).

Latkowski et al., "Keratinocyte Growth Factor and Keratin Gene Regulation", The Journal of Investigative Dermatology, 102(4):640, Abstract 700 (1994).

Leszcynski and Rose, "Loops in Globular Proteins: A Novel Category of Secondary Structure", Science, 234:849–855 (1985).

Leung et al., "Keratinocyte Growth Factor Enhances Colonic Mucus Production in Normal Rats and Rats Treated with Dextran Sulfate Sodium", Gastroenterology, 106(4):A617 (1994).

Malone et al., "Inhibition of Tumor Growth in Mice by an Analogue of Platelet Factor 4 That Lacks Affinity for Heparin and Retains Potent Angiostatic Activity", Cancer Research, 51:2077–2083 (1991).

Marchese et al., "Human Keratinocyte Growth Factor Activity on Proliferation and Differentiation of Human Keratinocytes: Differentiation Response Distinguishes KGF from EGF Family", Journal of Cellular Physiology, 144:326–332 (1990).

Marics et al., "Characterization of the HST–Related FGF.6 gene, a New Member of the Fibroblast Growth Factor Gene Family", Oncogene, 4:335–340 (1989).

Mason et al., "FGF–7 (keratinocyte growth factor) Expression During Mouse Development Suggests Roles in Myogenesis, Forebrain Regionalisation and Epithelial–mesenchymal interactions", Mechanisms of Development, 45:15–30 (1994).

McGarvey et al., "Keratinocyte Growth Factor and Receptor Expression in Benign and Malignant Prostate", Journal of Cellular Biochemistry, Supplement O(18D):232, Abstract Y117 (1994).

Mergia et al., "Structural Analysis of the Gene for Human Acidic Fibroblast Growth Factor", Biochem. Biophys. Res. Commun., 164(3):1121–1129 (1989).

Mild et al., "Expression cDNA Cloning of the KGF Receptor by Creation of a Transforming Autocrine Loop", Science, 251:72–75 (1991).

Miyamoto et al., "Molecular Cloning of a Novel Cytokine cDNA Encoding the Ninth Member of the Fibroblast Growth Factor Family, Which Has a Unique Secretion Property", Molecular and Cellular Biology, 13(7): 4251–4259, (1993).

Ohning et al., "Keratinocyte Growth Factor Promotes Healing of Acetic Acid–Induced Gastric Ulcers in Rats", Gastroenterology, 106(No. 4, Part 2):A150 (1994).

Ohning et al., "Keratinocyte Growth Factor Stimulates Proliferation and Alters Differentiation of the Gastric Fundic Mucosa in Rats", Gastroenterology, 106(No. 4, Part 2):A624 (1994).

Panos et al., "Intratracheal Instillation of Keratinocyte Growth Factor Prevents Hyperoxia–induced Mortality in Rats", Clinical Research, 42(3):426A (1994).

Panos et al., "Keratinocyte Growth Factor and Hepatocyte Growth Factor/Scatter Factor are Heparin–binding Growth Factors for Alveolar Type II Cells in Fibroblast–conditioned Medium", J. of Clin. Invest., 92(2):969–977 (1993).

Pekonen et al., "Differential Expression of Keratinocyte Growth Factor and its Receptor in the Human Uterus", Molecular and Cellular Endocrinology, 95:43–49 (1993).

Pierce et al., "Stimulation of All Epithelial Elements during Skin Regeneration by Keratinocyte Growth Factor", J. Exp. Med., 179:831–840 (1994).

Pinckard et al., "Factors Influencing the Immune Response: I. Effects of the Physical State of the Antigen and of Lymphoreticular Cell Proliferation of the Response to Intravenous Injection of Bovine Serum Albumin in Rabbits", Clin. Exp. Immunol., 2:331–341 (1967).

Presta et al., "Structure–Function Relationship of Basic Fibroblast Growth Factor: Site–Directed Mutagenesis of a Putative Heparin–Binding and Receptor–Binding Region", Biochemical and Biophysical Research Communications, 185(3):1098–1107 (1992).

Robbins et al., "Antibodies to Covalent Aggregates of Insulin in Blood of Insulin–Using Diabetic Patients", Diabetes, 36:838–845 (1987).

Ron et al., "Expression of Biologically Active Recombinant Keratinocyte Growth Factor", The Journal of Biological Chemistry, 268(4):2984–2988 (1993).

Rubin et al., "Purification and Characterization of a Newly Identified Growth Factor Specific for Epithelial Cells", Proc. Natl. Acad. Sci. USA, 86:802–806 (1989).

Rubin, J. S., "KGF is A Paracrine Mediator of Epithelial Cell Growth", Proc. Am. Assoc. Cancer Res. Annual Meeting, 34(O):588 (1993).

Russell et al., "Growth and Differentiation Effects of Keratinocyte Growth Factor (KGF) on Small Intestinal Mucosa", Gastroenterology, 112(4):A903 (1997).

Seno et al., "Stabilizing Basic Fibroblast Growth Factor Using Protein Engineering", Biochemical and Biophysical Research Communications, 151(2):701–706 (1998).

Slayden et al., "Keratinocyte Growth Factor (KGF) and KGF Receptor (KGFR) mRNAs in the Cervix, Placenta, and Decidual of Rhesus Macaques", Biology of Reproduction, 50(Suppl.1):121, Abstract 267 (1994).

Slayden et al., "Keratinocyte Growth Factor (KGF) Stimulates Epithelial Cell Proliferation in the Primate Oviduct and Vagina", Biology of Reproduction, 56(suppl. 1):103 (1997).

Smallwood et al., "Fibroblast growth factor (FGF) homologous factors: New members of the FGF family implicated in nervous system development", Proc. Natl. Acad. Sci. USA, 93:9850–9857 (1996).

Sotozono et al., "KGF and KGF Receptor mRNA Expression in Cultured Rabbit Corneal Cell", Invest. Ophthalmology & Visual Science, 35(4):1941, Abstract 3170–60 (1994).

Staiano–Coico et al., "Human Keratinocyte Growth Factor Effects in a Porcine Model of Epidermal Wound Healing", The Journal of Experimental Medicine, 178(3):865–878 (1993).

Strain et al., "Keratinocyte Growth Factor and Fibroblast Growth Factor Action on DNA Synthesis in Rat and Human Hepatocytes: Modulation by Heparin", Exp. Cell Research, 210(2):253–259 (1994).

Strydom et al., "Amino Acid Sequence of Bovine Brain Derived Class 1 Heparin–Binding Growth Factor", Biochemistry, 25(5):945–951 (1986).

Tagashira et al., "Cloning of Mouse FGF10 and Up–Regulation of its Gene Expression During Wound Healing", Gene, 197:399–404 (1997).

Tang et al., "Upregulation of Fibroblast Keratinocyte Growth Factor mRNA Expression by Interleukin–1–alpha, Interleukin–1–beta and Tumor Necrosis Factor–alpha", Journal of Investigative Dermatology, 102(4):528, Abstract 25 (1993).

Tsubol et al., "Keratinocyte Growth Factor (FGF–7) Stimulates Migration and Plasminogen Activator Activity of Normal Human Keratinocytes", The Journal of Investigative Dermatology, 101(1):49–53 (1993).

Tuan et al., "Dermal Fibroblasts Activate Keratinocyte Outgrowth on Collagen Gels", Journal of Cell Science, 107(8):2285–2289 (1994).

Ulich et al., "Keratinocyte Growth Factor is a Growth Factor for Type II Pneumocytes in Vivo", J. Clin. Invest., 93(3):1298–1306 (1994).

Ulich et al., "Keratinocyte Growth Factor is a Growth Factor for Mammary Epithelium in Vivo", Amer. J. of Pathology, 144(5):862–868 (1994).

Werner et al., "The Function of KGF in Morphogenesis of Epithelium and Reepithelialization of Wounds", Science, 266:819–822 (1994).

Werner et al., "Induction of Keratinocyte Growth Factor Expression is Reduced and Delayed During Wound Healing in the Genetically Diabetic Mouse", J. of Invest. Dermatol., 103(4):469–473 (1994).

Werner et al., "Large induction of Keratinocyte Growth Factor Expression in the Dermis during Wound Healing", Proc. Natl. Acad. Sci. USA, 89(15):6896–6900 (1992).

Wilkinson, David, "L–Serine Potentiates the Mitogenic Effects of Growth Factors on Cultured Human Keratinocytes", Journal of Investigative Dermatology 88(2):198–201 (1987).

Wilson et al., "EGF, HGF, KGF, and Human Corneal Epithelial Cell Motility, Proliferation, and Differentiation", Investigative Ophthalmology & Visual Science, 35(4):1319, Abstract 301 (1994).

Wilson et al., "Hepatocyte Growth Factor (HGF), Keratinocyte Growth Factor (KGF), Their Receptors and the Cells of the Cornea", The FASEB Journal, 7(3):A493, Abstract 2857 (1993).

Wu et al., "KGF Accelerates Ischemic Dermal Ulcer Healing in the Rabbit Ear", Surgical Forum, 44(O):704–706 (1993).

Yamasaki et al., "Structure and Expression of the Rat mRNA Encoding a Novel Member of the Fibroblast Growth Factor Family", J. Biol. Chem., 271(27):15918–15921 (1996).

Yan et al., "Sequence of Rat Keratinocyte Growth Factor (Heparin–Binding Growth Factor Type 7)", Chemical Abstracts, 118(15):abstract No. 140028v, Apr. 13, (1993).

Yan et al., "Sequence of Rat Keratinocyte Growth Factor (Heparin–Binding Growth Factor Type 7)", In Vitro Cell Dev. Biol., 27A(6):437–438 (1991).

Yi et al., "Keratinocyte Growth Factor Induces Pancreatic Ductal Epithelial Proliferation", Amer. Journal of Pathology, 145(1):80–85 (1994).

Yi et al., "Keratinocyte Growth Factor is a Growth Factor for Type II Pneumocyte in Vivo", Modern Pathology, 7(1):156A, Abstract 912 (1994).

Yoshida et al., Genomic Sequence of hst, a Transforming Gene Encoding a Protein Homologous to Fibroblast Growth Factors and the int–2–encoded Protein, Proc. Natl. Acad. Sci. USA, 84:7305–7309 (1987).

Zeeh et al., "Keratinocyte Growth Factor Improves Healing in an Experimental Model of Colitis in Rats", Gastroenterology, 106(4 Suppl):A853 (1994).

Zhan et al., "The Human FGF–5 Oncogene Encodes a Novel Protein Related to Fibroblast Growth Factors", Molecular and Cellular Biology, 8(8):3487–3495 (1988).

Zhu et al., "Three–Dimensional Structure of Acidic and Basic Fibroblast Growth Factors", Science, 251:90–93 (1991).

Yl et al., "Keratinocyte Growth Factor Ameliorates Radiation– and Bleomycin–Induced Lung Injury and Mortality," Am. J. Pathol. 149(6):1963–70 (1996).

* cited by examiner

FIG.1

```
5'-ATG TGG AAA TGG ATA CTG ACA CAT TGT GCC TCA GCC TTT CCC CAC-
    Met Trp Lys Trp Ile Leu Thr His Cys Ala Ser Ala Phe Pro His-

-CTG CCC GGC TGC TGC TGC TGC TTT TTG CTG TTC TTG GTG-
  Leu Pro Gly Cys Cys Cys Cys Phe Leu Leu Leu Phe Leu Val-

-TCT TCC GTC CCT GTC ACC TGC CAA GCC CTT GGT CAG GAC ATG GTG-
  Ser Ser Val Pro Val Thr Cys Gln Ala Leu Gly Gln Asp Met Val-

-TCA CCA GAG GCC ACC AAC TCT TCT TCC TCC TTC TCC TCT CCT-
  Ser Pro Glu Ala Thr Asn Ser Ser Ser Ser Phe Ser Ser Pro-

-TCC AGC GCG GGA AGG CAT GTG CGG AGC TAC AAT CAC CTT CAA GGA-
  Ser Ser Ala Gly Arg His Val Arg Ser Tyr Asn His Leu Gln Gly-

-GAT GTC CGC TGG AGA AAG CTA TTC TCT TTC ACC AAG TAC TTT CTC-
  Asp Val Arg Trp Arg Lys Leu Phe Ser Phe Thr Lys Tyr Phe Leu-

-AAG ATT GAG AAG AAC GGG AAG GTC AGC GGG ACC AAG AAG GAG AAC-
  Lys Ile Glu Lys Asn Gly Lys Val Ser Gly Thr Lys Lys Glu Asn-
```

FIG.1A

```
-TGC CCG TAC AGC ATC CTG GAG ATA ACA TCA GTA GAA ATC GGA GTT-
   Cys Pro Tyr Ser Ile Leu Glu Ile Thr Ser Val Glu Ile Gly Val

-GTT GCC GTC AAA GCC ATT AAC AGC AAC TAT TAC TTA GCC ATG AAC-
   Val Ala Val Lys Ala Ile Asn Ser Asn Tyr Tyr Leu Ala Met Asn

-AAG AAG GGG AAA CTC TAT GGC TCA AAA GAA TTT AAC AAT GAC TGT-
   Lys Lys Gly Lys Leu Tyr Gly Ser Lys Glu Phe Asn Asn Asp Cys

-AAG CTG AAG GAG AGG ATA GAG GAA AAT GGA TAC AAT ACC TAT GCA-
   Lys Leu Lys Glu Arg Ile Glu Glu Asn Gly Tyr Asn Thr Tyr Ala

-TCA TTT AAC TGG CAG CAT AAT GGG AGG CAA ATG TAT GTG GCA TTG-
   Ser Phe Asn Trp Gln His Asn Gly Arg Gln Met Tyr Val Ala Leu

-AAT GGA AAA GCT CCA AGG AGA GGA CAG AAA ACA CGA AGG AAA-
   Asn Gly Lys Ala Pro Arg Arg Gly Gln Lys Thr Arg Arg Lys

-AAC ACC TCT GCT CAC TTT CTT CCA ATG GTG GTA CAC TCA TAG-3'
   Asn Thr Ser Ala His Phe Leu Pro Met Val Val His Ser   *
```

FIG.2

```
5'- ATGTCCTACAATCACCTGCAGGGAGAGATGTCCGCTGGAGAAAGCTGTTCTCCTTCACCAAG-
    +----+----+----+----+----+----+----+----+----+----+----+----+
     M  S  Y  N  H  L  Q  G  D  V  R  W  R  K  L  F  S  F  T  K

-TACTTTCTCAAGATTGAAAAGAACGGCAAGGTCAGCGGGACCAAGAAGGAAAACTGTCCG-
    +----+----+----+----+----+----+----+----+----+----+----+----+
     Y  F  L  K  I  E  K  N  G  K  V  S  G  T  K  K  E  N  C  P-

-TACAGTATCCTAGAGATAACATCAGTGGAAATCGGAGTTGTTGCCGTCAAAGCCATTAAC-
    +----+----+----+----+----+----+----+----+----+----+----+----+
     Y  S  I  L  E  I  T  S  V  E  I  G  V  V  A  V  K  A  I  N-

-AGCAACTATTACTTAGCCATGAACAAGAAGGGGAAACTCTATGGCTCAAAAGAATTTAAC-
    +----+----+----+----+----+----+----+----+----+----+----+----+
     S  N  Y  Y  L  A  M  N  K  K  G  K  L  Y  G  S  K  E  F  N-
```

FIG.2A

```
-AATGACTGTAAACTGAAAGAGAGGATAGAGGAAAATGGATACAACACCTATGCATCTTTT-
-+---------+---------+---------+---------+---------+---------+-
 N  D  C  K  L  K  E  R  I  E  E  N  G  Y  N  T  Y  A  S  F

-AACTGGCAGCACAACGGCAGGCAAATGTATGTGGCATTGAATGGAAAAGGAGCTCCCAGG-
-+---------+---------+---------+---------+---------+---------+-
 N  W  Q  H  N  G  R  Q  M  Y  V  A  L  N  G  K  G  A  P  R

-AGAGGACAAAAAACAAGAAGGAAAAACACCTCCGCTCACTTCCTCCCCATGGTGGTCCAC-
-+---------+---------+---------+---------+---------+---------+-
 R  G  Q  K  T  R  R  K  N  T  S  A  H  F  L  P  M  V  V  H

-TCATAA -3'
-+-----
 S  *
```

FIG.3

```
5'- ATGTCTTCTCCTCCTCCTCTGCAGGTAGGCATGTGCGGAGCTACAATCACCTCCAGGAGAT-
     ----+---------+---------+---------+---------+---------+----
     M  S  S  P  S  S  A  G  R  H  V  R  S  Y  N  H  L  Q  G  D-

-GTCCGCTGGAGAAAGCTGTTCTCCTTCACCAAGTACTTTCTCAAGATTGAAAAGAACGGC-
     ----+---------+---------+---------+---------+---------+----
     V  R  W  R  K  L  F  S  F  T  K  Y  F  L  K  I  E  K  N  G-

-AAGGTCAGCGGGACCAAGAAGGAAAACTGTCCGTACAGTATCCTAGAGATAACATCAGTG-
     ----+---------+---------+---------+---------+---------+----
     K  V  S  G  T  K  K  E  N  C  P  Y  S  I  L  E  I  T  S  V-

-GAAATCGGAGTTGTTGCCGTCAAAGCCATTAACAGCAACTATTACTTAGCCATGAACAAG-
     ----+---------+---------+---------+---------+---------+----
     E  I  G  V  V  A  V  K  A  I  N  S  N  Y  Y  L  A  M  N  K-
```

FIG.3A

```
-AAGGGGAAACTCTATGGCTCAAAAGAATTTAACAATGACTGTAAACTGAAAGAGAGGATA-
 K  G  K  L  Y  G  S  K  E  F  N  N  D  C  K  L  K  E  R  I

-GAGGAAAAATGGATACAACACCTATGCATCTTTTAACTGGCAGCACAACGGCAGGCAAATG-
 E  E  N  G  Y  N  T  Y  A  S  F  N  W  Q  H  N  G  R  Q  M

-TATGTGGCATTGAATGGAAAAGGAGCTCCCAGGAGAGGACAAAAAACAAGAAGGAAAAAC-
 Y  V  A  L  N  G  K  G  A  P  R  R  G  Q  K  T  R  R  K  N

-ACCTCCGCTCACTTCCTCCCCATGGTGGTCCACTCATAA -3'
 T  S  A  H  F  L  P  M  V  V  H  S  *
```

FIG. 4

```
5'- ATGCTGGGTCAGGACATGGTTTCTCCGGAGGCTACCAACTCTAGTCCAGCAGCTTCTCC-
     M  L  G  Q  D  M  V  S  P  E  A  T  N  S  S  S  S  F  S -

-TCTCCTAGCTCTGCAGGTAGGCATGTGCGGAGCTACAATCACCTCCAGGGAGATGTCCGC-
    S  P  S  S  A  G  R  H  V  R  S  Y  N  H  L  Q  G  D  V  R -

-TGGAGAAAGCTGTTCTCCTTCACCAAGTACTTTCTCAAGATTGAAAAGAACGGCAAGGTC-
    W  R  K  L  F  S  F  T  K  Y  F  L  K  I  E  K  N  G  K  V -

-AGCGGGACCAAGAAGGAAAACTGTCCGTACAGTATCCTAGAGATAACATCAGTGGAAATC-
    S  G  T  K  K  E  N  C  P  Y  S  I  L  E  I  T  S  V  E  I -

-GGAGTTGTTGCCGTCAAAGCCATTAACAGCAACTATTACTTAGCCATGAACAAGAAGGGG-
    G  V  V  A  V  K  A  I  N  S  N  Y  Y  L  A  M  N  K  K  G -
```

FIG.4A

```
-AAACTCTATGGCTCAAAAGAATTAACAATGACTGTAAACTGAAAGAGAGGATAGAGGAA-
 K  L  Y  G  S  K  E  F  N  N  D  C  K  L  K  E  R  I  E  E

-AATGGATACAACACCTATGCATCTTTTAACTGGCAGCACAACGGCAGGCAAATGTATGTG-
 N  G  Y  N  T  Y  A  S  F  N  W  Q  H  N  G  R  Q  M  Y  V

-GCATTGAATGGAAAAGGAGCTCCCAGGCAGGGACAAAAACAAGAAGGAAAAACACCTCC-
 A  L  N  G  K  G  A  P  R  Q  G  Q  K  T  R  R  K  N  T  S

-GCTCACTTCCTCCCCATGGTGGTCCACTCATAA -3'
 A  H  F  L  P  M  V  V  H  S  *
```

KERATINOCYTE GROWTH FACTOR-2 PRODUCTS

This application is a 371 U.S.C. National Phase Filing of PCT/US97/18607, filed Oct. 15, 1997, which claims the benefit of U.S. Provisional Application No. 60/028,493, filed Oct. 15, 1996; U.S. Provisional Application No. 60/032,781, filed Dec. 6, 1996; and U.S. Provisional Application No. 60/033,046, filed Dec. 10, 1996, all of which are hereby incorporated by reference.

FIELD OF THE INVENTION

The present invention relates to the use of keratinocyte growth factor-2 (KGF-2) protein products to stimulate the proliferation, growth and differentiation of a variety of epithelial cells.

BACKGROUND OF THE INVENTION

The complex process of tissue generation and regeneration is mediated by a number of protein factors sometimes referred to as soft tissue growth factors. These molecules are generally released by one cell type and act to influence proliferation of other cell types (Rubin et al. (1989), *Proc. Nat'l. Acad. Sci. USA*, 86:802–806). There are also some growth factors released from cells that themselves have the capacity to respond to such growth factors. Some soft tissue growth factors are secreted by particular cell types and influence the proliferation, differentiation, and/or maturation of responsive cells in the development of multicellular organisms (Finch et al. (1989), *Science*, 245:752–755). In addition to their roles in developing organisms, some soft tissue growth factors are significant in the continued health and maintenance of more mature systems. For instance, in mammals there are many systems where rapid cell turnover occurs. Such systems include the skin and the gastrointestinal tract, both of which are comprised of epithelial cells. Included within this group of soft tissue growth factors is a protein family of fibroblast growth factors (FGFs).

The fibroblast growth factor (FGF) family is now known to consist of at least fourteen members, namely FGF-1 to FGF-10 and homologous factors FHF-1 to FHF-4, which share a relatedness among primary structures: basic fibroblast growth factor, bFGF (Abraham et al. (1986), *EMBO J.*, 5:2523–2528); acidic fibroblast growth factor, aFGF (Jaye et al. (1986), *Science*, 233:541–545); int-2 gene product, int-2 (Dickson & Peters (1987), *Nature*, 326:833); hst/kFGF (Delli-Bovi et al. (1987), *Cell*, 50:729–737 and Yoshida et al. (1987), *Proc. Natl. Acad. Sci. USA*, 84:7305–7309); FGF-5 (Zhan et al. (1988), *Mol. Cell. Biol.*, 8:3487–3495); FGF-6 (Marics et al. (1989), *Oncogene*, 4:335–340); keratinocyte growth factor, KGF (Finch et al. (1989), *Science*, 24:752–755); hisactophilin (Habazzettl et al. (1992), *Nature*, 359:855–858); FGF-9 (Miyamoto et al. (1993), *Mol. Cell Biol.*, 13(7):4251–4259); and fibroblast growth factor-10, also known as keratinocyte growth factor-2, KGF-2 (PCT patent application WO 96/25422), the disclosures of which are hereby incorporated by reference. More recently, four homologous factors (or "FHFs") were identified from the human retina by a combination of random cDNA sequencing, searches of existing sequence databases and homology-based polymerase chain reactions (Smallwood et al. (1996), *Proc. Natl. Acad. Sci. USA*, 93:9850–9857). It has been proposed that FHF-1, FHF-2, FHF-3 and FHF-4 should be designated as FGF-11, FGF-12, FGF-13 and FGF-14, respectively, in accordance with the recommendation of the Nomenclature Committee (Coulier et al. (1997), *Journal of Molecular Evolution*, 44:43–56, the disclosure of which is hereby incorporated by reference).

WO 96/25422 describes the cloning, expression and purification of full-length (with signal sequence, residues $Met^1$ to $Thr^{36}$ of SEQ ID NO:2) and mature (without signal sequence, residues $Cys^{37}$ to $Ser^{208}$ of SEQ ID NO:2) KGF-2 in a bacterial expression system (e.g., *E. coli*) and eukaryotic expression systems (e.g., baculovirus and COS cells). This reference further teaches that KGF-2 might be useful to stimulate cell growth and proliferation for new blood vessel growth or angiogenesis, the prevention of hair loss, the healing of dermal wounds and the differentiation of muscle cells, nervous tissue, prostate cells and lung cells.

Much remains to be learned regarding KGF-2, including modifications which can be made thereto to generate variant(s) and derivatives which retain some or all of the biological activity of KGF-2. Generally, the effects of any specific amino acid change or chemical derivatization upon biological activity of a protein will vary depending upon a number of factors, including whether or not modifications affect the three-dimensional structure or the receptor binding region of the protein. As neither the three-dimensional structure nor the receptor binding region of KGF-2 has been published, the knowledge within the art does not permit generalization about the effects of specific amino acid modifications or chemical derivatization to KGF-2.

It is the object of this invention to provide variants and derivatives of KGF-2 that retain some or all of the biological activity of KGF-2.

SUMMARY OF THE INVENTION

The present invention is directed to KGF-2 protein product(s), as defined below. These KGF-2 protein product(s) have general applicability and may retain some or all of the biological activity of KGF-2.

In one aspect, a variant(s) of KGF-2 is produced by recombinant genetic engineering techniques. In an alternative embodiment, a variant(s) of KGF-2 is synthesized by chemical techniques, or a combination of the recombinant and chemical techniques A variant(s) of KGF-2 may be made in glycosylated or non-glycosylated form.

Yet another aspect of the present invention includes the various polynucleotides encoding a variant(s) of KGF-2. Each such nucleic acid sequence may be used in the expression of a variant(s) of KGF-2 in a eukaryotic or prokaryotic host cell. The polynucleotides may also be used in cell therapy or gene therapy applications.

A further aspect of the present invention involves vectors containing the polynucleotides encoding a variant(s) of KGF-2 operatively linked to amplification and/or expression control sequences.

A still further aspect of the present invention pertains to both prokaryotic and eukaryotic host cells containing recombinant polynucleotides encoding variant(s) of KGF-2.

In another aspect, the present invention further includes the recombinant production of a variant(s) of KGF-2 wherein recombinant host cells are grown in a suitable nutrient medium and wherein a variant(s) of KGF-2 expressed by the cells is, optionally, isolated from the host cells and/or the nutrient medium.

A still further aspect of the present invention includes KGF-2 protein(s), as defined below, attached to a water soluble polymer. For example, a variant(s) of KGF-2 may be conjugated to one or more polyethylene glycol molecules in order to improve pharmacokinetic performance by increasing the molecule's apparent molecular weight.

Another aspect of the present invention includes pharmaceutical compositions containing a variant(s) of KGF-2, or chemical derivative(s) of KGF-2 protein(s). Typically, a variant(s) of KGF-2 may be formulated in association with pharmaceutically acceptable vehicles. A variety of other formulation materials may be used to facilitate the manufacture, storage, handling, delivery and/or efficacy of a variant(s) of KGF-2.

Yet another aspect relates to methods of modulating the growth and differentiation of epithelial cells. Specifically, a patient in need of stimulation (including cytoprotection, proliferation and/or differentiation) of epithelial cells will be administered a therapeutically-effective or prophylactically-effective amount of a variant(s) of KGF-2 and/or a chemical derivative of KGF-2 protein(s).

Additional aspects and advantages of the invention will be apparent to those skilled in the art upon consideration of the following description, which details the practice of the present invention.

BRIEF DESCRIPTION OF THE FIGURES

Numerous aspects and advantages of the present invention will become apparent upon review of the Figures, wherein:

FIG. 1 depicts a cDNA sequence (SEQ ID NO:1) encoding full-length, recombinant human KGF-2. Also depicted is the amino acid sequence (SEQ ID NO:2) of full-length, recombinant human KGF-2. The initial 36 amino acid residues ($Met^1$ to $Thr^{36}$) represent the putative leader sequence of full-length KGF-2, and residues $Cys^{37}$ to $Ser^{208}$ of SEQ ID NO:2 represent mature KGF-2. The full-length and mature forms are collectively termed "KGF-2".

FIG. 2 depicts a cDNA sequence (SEQ ID NO:3) encoding dN29 hFGF10. Also depicted is the amino acid sequence (SEQ ID NO:4) of dN29 hFGF10.

FIG. 3 depicts a cDNA sequence (SEQ ID NO:5) encoding dN20 hFGF10. Also depicted is the amino acid sequence (SEQ ID NO:6) of dN20 hFGF10.

FIG. 4 depicts a cDNA sequence (SEQ ID NO:7) encoding hFGF10 R149Q. Also depicted is the amino acid sequence (SEQ ID NO:8) of hFGF10 R149Q.

DETAILED DESCRIPTION OF THE INVENTION

KGF-2 Protein(s)

In accordance with the terms of this invention, by the term "KGF-2 protein(s)" is meant the protein defined by amino acids $Cys^{37}$ to $Ser^{208}$ of SEQ ID NO:2 (mature KGF-2) and variant proteins thereof. The term "KGF-2 protein(s)" thus includes a protein in which one or more amino acid residues have been deleted from ("deletion variant(s)"), inserted into ("addition variant(s)"), and/or substituted for ("substitution variant(s)") residues within the amino acid sequence of SEQ ID NO:2 and which retains biological activity. Thus, while the descriptions below of protein modifications refer to mature KGF-2, it does not preclude additional modifications thereto.

The term "biological activity" as used herein means that a KGF-2 protein(s) possesses some but not necessarily all the same properties of (and not necessarily to the same degree as) mature KGF-2. The selection of the particular properties of interest depends upon the desired use of the desired KGF-2 protein(s).

It will be appreciated by those skilled in the art that many combinations of deletions, insertions, and substitutions can be made, provided that the final protein is biologically active. There are two principal variables in the construction of amino acid sequence variant(s): the location of the mutation site and the nature of the mutation. In designing a variant(s), the location of the mutation site and the nature of the mutation will depend on the biochemical characteristic(s) to be modified. Mutation sites can be modified individually or in series, e.g., by (1) deleting the target amino acid residue, (2) inserting amino acid residues adjacent to the located site or (3) substituting first with conservative amino acid choices and, depending upon the results achieved, then with more radical selections.

Amino acid sequence deletions generally range from about 40 amino acid residues, from about 30 amino acids, from about 20 amino acids, and typically from about 1 to 10 residues. Deletions within the amino acid sequence of mature KGF-2 may be made, for example, in regions of low homology with the sequences of other members of the FGF family. Deletions within the amino acid sequence of mature KGF-2 in areas of substantial homology with the sequences of other members of the FGF family will be more likely to significantly modify the biological activity. The number of total deletions and/or consecutive deletions preferably will be selected so as to preserve the tertiary structure of mature KGF-2 (amino acids $Cys^{37}$ to $Ser^{208}$ of SEQ ID NO:2) in the affected domain, e.g., cysteine crosslinking.

Amino acid sequence additions may include amino- and/or carboxyl-terminal fusions ranging in length from one residue to one hundred or more residues, as well as internal intrasequence insertions of single or multiple amino acid residues. Internal additions may range preferably from about 1 to 10 amino acid residues, more preferably from about 1 to 5 amino acid residues, and most preferably from about 1 to 3 amino acid residues. Additions within the amino acid sequence of mature KGF-2 may be made in regions of low homology with the sequences of other members of the FGF family. Additions within the amino acid sequence of mature KGF-2 in areas of substantial homology with the sequences of other members of the FGF family will be more likely to significantly modify the biological activity. Insertions or additions preferably include amino acid sequences derived from the sequences of other FGF family members.

An amino-terminus addition is contemplated to include the addition of a methionine (for example, as an artifact of the direct expression in bacterial recombinant cell culture) or an amino acid residue or sequence of mature KGF-2. A further example of an N-terminal addition includes the fusion of a signal sequence to the N-terminus of mature KGF-2 in order to facilitate the secretion of protein from recombinant host cells. Such signal sequences generally will be obtained from and thus be homologous to the intended host cell species. Included within the scope of this invention is the native signal sequence, for example, the native signal sequence of the protein defined by amino acids $Met^1$ to $Thr^{36}$ of SEQ ID NO:2 or a heterologous signal sequence. A heterologous signal sequence selected should be one that is recognized and processed (i.e., cleaved by a signal peptidase) by the host cell. For prokaryotic host cells that do not recognize and process the native signal sequence, the signal sequence may be substituted by a prokaryotic signal sequence selected, for example, from the group of the alkaline phosphatase, penicillinase or heat-stable enterotoxin II leaders. For yeast secretion, the signal sequence may be selected, for example, from the group of the yeast invertase, alpha factor or acid phosphatase leader sequences. In mammalian cell expression specifically, signal sequences of full-length KGF-2 or of other FGF family members (e.g., KGF) may be suitable.

An example of a carboxy-terminus addition includes chimeric proteins comprising the fusion of KGF-2 with all or part of the constant domain of the heavy or light chain of human immunoglobulin. Such chimeric polypeptides are preferred wherein the immunoglobulin portion comprises all the domains except the first domain of the constant region of the heavy chain of a human immunoglobulin such as IgG, IgA, IgM or IgE, especially IgG, e.g., IgG1 or IgG3. A skilled artisan will appreciate that any amino acid of the immunoglobulin portion can be deleted or substituted by one or more amino acids, or one or more amino acids can be added as long as the KGF-2 portion still stimulates epithelial cells and the immunoglobulin portion shows one or more of its characteristic properties.

Another group of variant(s) is amino acid substitution variant(s) of the amino acid sequence of mature KGF-2. These variant(s) have at least one amino acid residue in the sequence of $Cys^{37}$ to $Ser^{208}$ of SEQ ID NO:2 removed and a different residue inserted in its place. Substitution variant(s) include allelic variant(s), which are characterized by naturally-occurring nucleotide sequence changes in the species population that may or may not result in an amino acid change. One skilled in the art can use any information known about the binding or active site of the polypeptide in the selection of possible mutation sites.

One method for identifying amino acid residues or regions for mutagenesis is called "alanine scanning mutagenesis", as described by Cunningham and Wells (1989), *Science*, 244:1081–1085, the disclosure of which is hereby incorporated by reference. In this method, an amino acid residue or group of target residues is identified (e.g., charged residues such as Arg, Asp, His, Lys, and Glu) and replaced by a neutral or negatively-charged amino acid (most preferably alanine or polyalanine) to effect the interaction of the amino acids with the surrounding aqueous environment in or outside the cell. Those domains demonstrating functional sensitivity to the substitutions are then refined by introducing additional or alternate residues at the sites of substitution. Thus, the site for introducing an amino acid sequence modification is predetermined and, to optimize the performance of a mutation at a given site, alanine scanning or random mutagenesis may be conducted and the variant(s) may be screened for the optimal combination of desired activity and degree of activity.

The sites of greatest interest for substitutional mutagenesis include sites in which particular residues within amino acids $Cys^{37}$ to $Ser^{208}$ of SEQ ID NO:2 are substantially different from various species or other FGF family members in terms of side-chain bulk, charge, and/or hydrophobicity. Other sites of interest include those in which particular residues within amino acids $Cys^{37}$ to $Ser^{208}$ of SEQ ID NO:2, are identical among various species or other FGF family members. Such positions are generally important for the biological activity of a protein. Accordingly, a skilled artisan would appreciate that initially these sites should be modified by substitution in a relatively conservative manner.

Such conservative substitutions are shown in Table 1 under the heading of "Preferred Substitutions". If such substitutions result in a change in biological activity, then more substantial changes (Exemplary Substitutions) may be introduced and/or other additions/deletions may be made and the resulting products screened.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

In making such changes of an equivalent nature, the hydropathic index of amino acids may be considered. The importance of the hydropathic amino acid index in conferring interactive biological function on a protein is generally understood in the art (Kyte and Doolittle (1982), *J. Mol. Biol.*, 157:105–131, the disclosure of which is incorporated herein by reference). It is known that certain amino acids may be substituted for other amino acids having a similar hydropathic index or score and still retain a similar biological activity.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, the disclosure of which is incorporated herein by reference, states that the greatest local average hydrophilicity of a protein, as governed by the hydrophilicity of its adjacent amino acids, correlates with its immunogenicity and antigenicity, i.e., with a biological property of the protein.

U.S. Pat. No. 4,554,101 also teaches the identification and preparation of epitopes from primary amino acid sequences on the basis of hydrophilicity. Through the methods disclosed in U.S. Pat. No. 4,554,101 a skilled artisan would be able to identify epitopes, for example, within the amino acid sequence of KGF-2. These regions are also referred to as "epitopic core regions". Numerous scientific publications have been devoted to the prediction of secondary structure, and to the identification of epitopes, from analyses of amino acid sequences (Chou and Fasman (1974), *Biochemistry*, 13(2):222–245; Chou and Fasman (1974), *Biochemistry*, 13(2):211–222; Chou and Fasman (1978), *Adv. Enzymol. Relat. Areas Mol. Biol.*, 47:45–148; Chou and Fasman (1978), *Ann. Rev. Biochem.*, 47:251–276 and Chou and Fasman (1979), *Biophys. J.*, 26:367–384, the disclosures of which are incorporated herein by reference). Moreover, computer programs are currently available to assist with predicting antigenic portions and epitopic core regions of proteins. Examples include those programs based upon the Jameson-Wolf analysis (Jameson and Wolf (1988), *Comput. Appl. Biosci.*, 4(1):181–186 and Wolf et al. (1988), *Comput. Appl. Biosci.*, 4(1):187–191, the disclosures of which are incorporated herein by reference); the program PepPlot® (Brutlag et al. (1990), *CABS*, 6:237–245 and Weinberger et al. (1985), *Science*, 228:740–742, the disclosures of which are incorporated herein by reference); and other new programs for protein tertiary structure prediction (Fetrow and Bryant (1993), *BIOTECHNOLOGY*, 11:479–483, the disclosure of which is incorporated herein by reference).

In contrast, substantial modifications in the functional and/or chemical characteristics of the amino acids $Cys^{37}$ to $Ser^{208}$ of SEQ ID NO:2 may be accomplished by selecting substitutions that differ significantly in their effect on maintaining (a) the structure of the polypeptide backbone in the area of the substitution, for example, as a sheet or helical conformation, (b) the relative charge or hydrophobicity of the protein at the target site or (c) the bulk of the side chain. Naturally-occurring residues are divided into groups based on common side chain properties 1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these groups for another. Such substituted residues may be introduced into regions of amino acids $Cys^{37}$ to $Ser^{208}$ of SEQ ID NO:2 that, for example, are homologous with regions of other FGF family members or into the non-homologous regions of the protein.

In a specific embodiment, a variant polypeptide will preferably be substantially homologous to amino acids $Cys^{37}$ to $Ser^{208}$ of SEQ ID NO:2. The term "substantially homologous", as used herein, means having a degree of homology (i.e., identity of amino acid residues) to amino acids $Cys^{37}$ to $Ser^{208}$ of SEQ ID NO:2 in excess of eighty percent (80%); preferably, in excess of ninety percent (90%); more preferably, in excess of ninety-five percent (95%); and most preferably, in excess of ninety-nine percent (99%). The percentage of homology as described herein is calculated as the percentage of amino acid residues found in the smaller of the two sequences which align with identical amino acid residues in the sequence being compared when four gaps in a length of 100 amino acids may be introduced to assist in that alignment, as set forth by Dayhoff (1972), in *Atlas of Protein Sequence and Structure*, 5:124, National Biochemical Research Foundation, Washington, D.C., the disclosure of which is hereby incorporated by reference. Also included as substantially homologous are variant(s) of the amino acids $Cys^{37}$ to $Ser^{208}$ of SEQ ID NO:2 which may be isolated by virtue of cross-reactivity with antibodies to amino acids $Cys^{37}$ to $Ser^{208}$ of SEQ ID NO:2, or whose genes may be isolated through hybridization with the DNA of SEQ ID NO:1 or with segments thereof.

A first class of variant(s) is a group of deletion variants of $Cys^{37}$ to $Ser^{208}$ of SEQ ID NO:2. These variants include $R_1$-[$Asn^{71}$-$Pro^{203}$]-$R_2$—COOH proteins, and further include an amino acid sequence comprising $NH_2$-[$His^{72}$-$Ser^{208}$]-COOH (also referred to as ΔN35 KGF-2), $NH_2$-[$Leu^{73}$-$Ser^{208}$]-COOH (also referred to as ΔN36 KGF-2), $NH_2$-[$Gln^{74}$-$Ser^{208}$]-COOH (also referred to as ΔN37 KGF-2), $NH_2$-[$Gly^{75}$-$Ser^{208}$]-COOH (also referred to as ΔN38 KGF-2), $NH_2$-[$Asp^{76}$-$Ser^{208}$]-COOH (also referred to as ΔN39 KGF-2), $NH_2$-[$Val^{77}$-$Ser^{208}$]-COOH (also referred to as ΔN40 KGF-2) and $NH_2$-[$Arg^{78}$-$Ser^{208}$]-COOH (also referred to as ΔN41 KGF-2), in which each may be N-terminally methionylated or non-methionylated, provided however that $Cys^{37}$ to $Ser^{208}$ of SEQ ID NO:2 is excluded.

By "$R_1$-[$Asn^{71}$-$Pro^{203}$]-$R_2$—COOH" is meant a group of deletion variant(s), wherein [$Asn^{71}$-Pro203] represents residues 71 through 203 of SEQ ID NO:2; wherein $R_1$ represents a methionylated or nonmethionylated amine group of $Asn^{71}$ or of amino-terminus amino acid residue(s) selected from the group:

Tyr

Ser-Tyr

Arg-Ser-Tyr

Val-Arg-Ser-Tyr (SEQ ID NO:9),

His-Val-Arg-Ser-Tyr (SEQ ID NO:10),

Arg-His-Val-Arg-Ser-Tyr (SEQ ID NO:11),

Gly-Arg-His-Val-Arg-Ser-Tyr (SEQ ID NO:12),

Ala-Gly-Arg-His-Val-Arg-Ser-Tyr (SEQ ID NO:13),

Ser-Ala-Gly-Arg-His-Val-Arg-Ser-Tyr (SEQ ID NO:14),

Ser-Ser-Ala-Gly-Arg-His-Val-Arg-Ser-Tyr (SEQ ID NO:15),

Pro-Ser-Ser-Ala-Gly-Arg-His-Val-Arg-Ser-Tyr (SEQ ID NO:16),

Ser-Pro-Ser-Ser-Ala-Gly-Arg-His-Val-Arg-Ser-Tyr (SEQ ID NO:17),

Ser-Ser-Pro-Ser-Ser-Ala-Gly-Arg-His-Val-Arg-Ser-Tyr (SEQ ID NO:18),

Phe-Ser-Ser-Pro-Ser-Ser-Ala-Gly-Arg-His-Val-Arg-Ser-Tyr (SEQ ID NO:19),

Ser-Phe-Ser-Ser-Pro-Ser-Ser-Ala-Gly-Arg-His-Val-Arg-Ser-Tyr (SEQ ID NO:20),

Ser-Ser-Phe-Ser-Ser-Pro-Ser-Ser-Ala-Gly-Arg-His-Val-Arg-Ser-Tyr (SEQ ID NO:21),

Ser-Ser-Phe-Ser-Ser-Pro-Ser-Ser-Ala-Gly-Arg-His-Val-Arg-Ser-Tyr (SEQ ID NO:22),

Ser-Ser-Ser-Phe-Ser-Ser-Pro-Ser-Ser-Ala-Gly-Arg-His-Val-Arg-Ser-Tyr (SEQ ID NO:23),

Ser-Ser-Ser-Ser-Phe-Ser-Ser-Pro-Ser-Ser-Ala-Gly-Arg-His-Val-Arg-Ser-Tyr (SEQ ID NO:24),

Asn-Ser-Ser-Ser-Ser-Ser-Phe-Ser-Ser-Pro-Ser-Ser-Ala-Gly-Arg-His-Val-Arg-Ser-Tyr (SEQ ID NO:25),

Thr-Asn-Ser-Ser-Ser-Ser-Ser-Phe-Ser-Ser-Pro-Ser-Ser-Ala-Gly-Arg-His-Val-Arg-Ser-Tyr (SEQ ID NO:26),

Ala-Thr-Asn-Ser-Ser-Ser-Ser-Ser-Phe-Ser-Ser-Pro-Ser-Ser-Ala-Gly-Arg-His-Val-Arg-Ser-Tyr (SEQ ID NO:27),

Glu-Ala-Thr-Asn-Ser-Ser-Ser-Ser-Ser-Phe-Ser-Ser-Pro-Ser-Ser-Ala-Gly-Arg-His-Val-Arg-Ser-Tyr (SEQ ID NO:28),

Pro-Glu-Ala-Thr-Asn-Ser-Ser-Ser-Ser-Ser-Phe-Ser-Ser-Pro-Ser-Ser-Ala-Gly-Arg-His-Val-Arg-Ser-Tyr (SEQ ID NO:29),

Ser-Pro-Glu-Ala-Thr-Asn-Ser-Ser-Ser-Ser-Ser-Phe-Ser-Ser-Pro-Ser-Ser-Ala-Gly-Arg-His-Val-Arg-Ser-Tyr (SEQ ID NO:30),

Val-Ser-Pro-Glu-Ala-Thr-Asn-Ser-Ser-Ser-Ser-Ser-Phe-Ser-Ser-Pro-Ser-Ser-Ala-Gly-Arg-His-Val-Arg-Ser-Tyr (SEQ ID NO:31),

Met-Val-Ser-Pro-Glu-Ala-Thr-Asn-Ser-Ser-Ser-Ser-Ser-Phe-Ser-Ser-Pro-Ser-Ser-Ala-Gly-Arg-His-Val-Arg-Ser-Tyr (SEQ ID NO:32),

Asp-Met-Val-Ser-Pro-Glu-Ala-Thr-Asn-Ser-Ser-Ser-Ser-Phe-Ser-Ser-Pro-Ser-Ser-Ala-Gly-Arg-His-Val-Arg-Ser-Tyr (SEQ ID NO:33),

Gln-Asp-Met-Val-Ser-Pro-Glu-Ala-Thr-Asn-Ser-Ser-Ser-Ser-Phe-Ser-Ser-Pro-Ser-Ser-Ala-Gly-Arg-His-Val-Arg-Ser-Tyr (SEQ ID NO:34),

Gly-Gln-Asp-Met-Val-Ser-Pro-Glu-Ala-Thr-Asn-Ser-Ser-Ser-Ser-Phe-Ser-Ser-Pro-Ser-Ser-Ala-Gly-Arg-His-Val-Arg-Ser-Tyr (SEQ ID NO:35),

Leu-Gly-Gln-Asp-Met-Val-Ser-Pro-Glu-Ala-Thr-Asn-Ser-Ser-Ser-Ser-Phe-Ser-Ser-Pro-Ser-Ser-Ala-Gly-Arg-His-Val-Arg-Ser-Tyr (SEQ ID NO:36),

Ala-Leu-Gly-Gln-Asp-Met-Val-Ser-Pro-Glu-Ala-Thr-Asn-Ser-Ser-Ser-Ser-Phe-Ser-Ser-Pro-Ser-Ser-Ala-Gly-Arg-His-Val-Arg-Ser-Tyr (SEQ ID NO:37),

Gln-Ala-Leu-Gly-Gln-Asp-Met-Val-Ser-Pro-Glu-Ala-Thr-Asn-Ser-Ser-Ser-Ser-Phe-Ser-Ser-Pro-Ser-Ser-Ala-Gly-Arg-His-Val-Arg-Ser-Tyr (SEQ ED NO:38), or

Cys-Gln-Ala-Leu-Gly-Gln-Asp-Met-Val-Ser-Pro-Glu-Ala-Thr-Asn-Ser-Ser-Ser-Ser-Ser-Phe-Ser-Ser-Pro-Ser-Ser-Ala-Gly-Arg-His-Val-Arg-Ser-Tyr (SEQ ID NO:39), and, wherein $R_2$ represents a carboxy group of $Pro^{203}$ or of carboxy-terminal amino acid residues of:

Met

Met-Val-Val

Met-Val-Val-His (SEQ ID NO:40), or

Met-Val-Val-His-Ser (SEQ ID NO:41), provided however, that $R_1$ and $R_2$ are not selected so as to reconstruct $Cys^{37}$ to $Ser^{208}$ of SEQ ID NO:2.

Exemplary substitutions of KGF-2 and of variant(s) of KGF-2 (particularly $R_1$-[$Asn^{71}$-$Pro^{203}$]-$R_2$—COOH proteins, and more particularly ΔN36 KGF-2, ΔN35 KGF-2, ΔN34 KGF-2, ΔN33 KGF-2, ΔN32 KGF-2, ΔN31 KGF-2, ΔN30 KGF-2, ΔN29 KGF-2, ΔN28 KGF-2, ΔN27 KGF-2 and ΔN26 KGF-2, either methionylated or nonmethionylated) are set forth in the following table:

Preferred variant(s) within this class include the following molecules: ΔN36 KGF-2; ΔN35 KGF2; $NH_2$-[$Asn^{71}$-$Ser^{208}$]-COOH (also referred to as ΔN34 KGF-2); $NH_2$-Tyr-[$Asn^{71}$-$Ser^{208}$]-COOH (also referred to as ΔN33 KGF-2); $NH_2$-Ser-Tyr-[$Asn^{71}$-$Ser^{208}$]-COOH (also referred to as ΔN32 KGF-2); $NH_2$-Arg-Ser-Tyr-[$Asn^{71}$-$Ser^{208}$]-COOH (also referred to as ΔN31 KGF-2); $NH_2$-Val-Arg-Ser-Tyr-[$Asn^{71}$-$Ser^{208}$]-COOH (also referred to as ΔN30 KGF-2); $NH_2$-His-Val-Arg-Ser-Tyr-[$Asn^{71}$-$Ser^{208}$]-COOH (also referred to as ΔN29 KGF-2); $NH_2$-Arg-His-Val-Arg-Ser-Tyr-[$Asn^{71}$-$Ser^{208}$]-COOH (also referred to as ΔN28 KGF-2); $NH_2$-Gly-Arg-His-Val-Arg-Ser-Tyr-[$Asn^{71}$-$Ser^{208}$]-COOH (also referred to as ΔN27 KGF-2); and $NH_2$-Ala-Gly-Arg-His-Val-Arg-Ser-Tyr-[$Asn^{71}$-$Ser^{208}$]-COOH (also referred to as ΔN26 KGF-2), either methionylated or non-methionylated.

A second class of variant(s) is a group of substitution, deletion or addition variant(s) of KGF-2 and/or of the first class of KGF-2 variant(s), described above, having a region corresponding to $Asn^{168}$ to $Met^{176}$ of SEQ ID NO:2 wherein at least one amino acid residue within the region corresponding to $Asn^{168}$ to $Met^{176}$ of SEQ ID NO:2 is deleted or substituted with a non-native amino acid, or a non-native amino acid is added within the region corresponding to $Asn^{168}$ to $Met^{176}$ of SEQ ID NO:2; this region is unique among the FGF family and contains residues ($Trp^{169}$ and $His^{171}$) which may predominantly confer binding specificity and residues ($Gly^{173}$ and $Met^{176}$) which may predominantly stabilize the structure to the region. In a specific embodiment, the region corresponding to $Asn^{168}$ to $Met^{176}$ is deleted or replaced with the following sequence: $NH_2$-Ala-Lys-Trp-Thr-His-Asn-Gly-Gly-Glu-Met-COOH, which is the sequence of a putative receptor binding region of KGF.

A third class of variant(s) is a group of deletion or substitution variant(s) of KGF-2 and/or of the first class of KGF-2 variant(s) and/or of the second class of KGF-2 variant(s), described above, having a region corresponding to $Phe^{85}$ to $Ser^{198}$ of SEQ ID NO:2 wherein at least one neutral or positively charged amino acid residue within the region corresponding to $Phe^{85}$ to $Ser^{198}$ of SEQ ID NO:2 is deleted or substituted with a neutral residue or negatively charged residue selected to effect a charge-change protein with a reduced positive charge. Preferred residues for modification are residues corresponding to $Phe^{85}$, $Thr^{86}$, $Asn^{159}$, $Gly^{182}$, $Arg^{187}$, $Asn^{196}$, $Thr^{197}$, $Ser^{198}$ of SEQ ID NO:2, with residues $Thr^{86}$, $Gly^{182}$, $Arg^{187}$ and $Asn^{196}$ being more preferred. Preferred amino acids for substitution include alanine, glutamic acid, aspartic acid, glutamine, asparagine, glycine, valine, leucine, isoleucine, serine and threonine; with alanine, glutamic acid, glutamine, aspartic acid and asparagine being more preferred; and with alanine being most preferred.

A fourth class of variant(s) is a group of substitution variant(s) of KGF-2 and/or of the first class of KGF-2 variant(s) and/or of the second class of KGF-2 variant(s) and/or of the third class of KGF-2 variant(s), described above, having a region corresponding to a putative surface loop-forming region, $Asn^{160}$ to $Thr^{164}$ of SEQ ID NO:2, wherein at least one amino acid having a higher loop forming potential is substituted for at least one amino acid having a lower loop forming potential within the region corresponding to $Asn^{160}$ to $Thr^{164}$ of SEQ ID NO:2. The non-native amino acid is selected for its higher loop-forming potential in order to stabilize this area of the protein. Amino acids having relatively high loop-forming potential include glycine, proline, tyrosine, aspartic acid, asparagine, and serine. Leszcynski et al, Science, 234, 849–855 (1986) (relative values of loop-forming potential assigned on the basis of frequency of appearance in loop structures of naturally occurring molecules). Preferably, a different amino acid having higher loop-forming potential replaces a threonine residue corresponding to $Thr^{164}$ of SEQ ID NO:2 in the loop-forming sequence.

A fifth class of variant(s) is a group of substitution variant(s) of KGF-2 and/or of the first class of KGF-2 variant(s) and/or of the second class of KGF-2 variant(s) and/or of the third class of KGF-2 variant(s) and/or of the fourth class of KGF-2 variant(s), described above, having amino acid residues corresponding to $Cys^{37}$, $Cys^{106}$ or $Cys^{150}$ of SEQ ID NO:2 wherein at least one naturally-occurring cysteine residue at a position corresponding to position 37, 106 or 150 of SEQ ID NO:2 is deleted or substituted with a non-native amino acid residues (e.g., Ala, Leu, or Ser).

A sixth class of variant(s) is a group of substitution or deletion variant(s) of KGF-2 and/or of the first class of KGF-2 variant(s) and/or of the second class of KGF-2 variant(s) and/or of the third class of KGF-2 variant(s) and/or of the fourth class of KGF-2 variant(s) and/or of the fifth class of KGF-2 variant(s), described above, having at least one N-linked or O-linked glycosylation site corresponding to an N-linked or O-linked glycosylation site within $Cys^{37}$ to $Ser^{208}$ of SEQ ID NO:2. Such variant(s) have at least one amino acid within the N-linked or O-linked glycosylation site within the region corresponding to an N-linked or O-linked glycosylation site within $Cys^{37}$ to $Ser^{208}$ of SEQ ID NO:2 deleted or substituted with a non-native amino acid, to modify the N-linked or O-linked glycosylation site and generate a protein with altered glycosylation. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. Proven or predicted asparagine residues exist at positions 51 and 196 of amino acids $Cys^{37}$ to $Ser^{208}$ of SEQ ID NO:2. A variety of amino acid substitutions or deletions may be made to modify N-linked or O-linked glycosylation sites.

A seventh class of variant(s) is a group of addition variant(s) of KGF-2 and/or of the first class of KGF-2 variant(s) and/or of the second class of KGF-2 variant(s) and/or of the third class of KGF-2 variant(s) and/or of the fourth class of KGF-2 variant(s) and/or of the fifth class of KGF-2 variant(s) and/or of the sixth class of KGF-2 variant(s) described above, wherein putative cleavage sites $Asn^{128}$-$Gly^{129}$ and/or $Asn^{141}$-$Gly^{142}$ are modified by a substitution of an amino acid (e.g., Gln or Ser) for the $Asn^{128}$ and/or $Asn^{141}$.

A eighth class of variant(s) is a group of addition variant(s) of KGF-2 and/or of the first class of KGF-2 variant(s) and/or of the second class of KGF-2 variant(s) and/or of the third class of KGF-2 variant(s) and/or of the fourth class of KGF-2 variant(s) and/or of the fifth class of KGF-2 variant(s) and/or of the sixth class of KGF-2 variant(s) and/or of the seventh class of KGF-2 variant(s), described above, wherein fused to the C-terminus of one of the aforementioned proteins is an immunoglobulin portion comprising at least one domain of the constant region of the heavy chain of human immunoglobulin (however, generally excluding the first domain) such as IgG, IgA, IgM or IgE, especially IgG, e.g., IgG1 or IgG3.

Exemplary substitutions of KGF-2 and of variant(s) of KGF-2 (particularly $R_1$-[$Asn^{71}$-$Pro^{203}$]-COOH proteins, and more particularly ΔN36 KGF-2, ΔN35 KGF-2, ΔN34 KGF-2, ΔN33 KGF-2, ΔN32 KGF-2, ΔN31 KGF-2, ΔN30 KGF-2, ΔN29 KGF-2, ΔN28 KGF-2, ΔN27 KGF-2 and ΔN26 KGF-2, either methionylated or nonmethionylated) are set forth in the following table:

TABLE 2

| Original residue | Preferred Substitution |
| --- | --- |
| $Asn^{71}$ | Arg, Asp, Glu, Lys |
| $Leu^{82}$ | Gly |
| $Phe^{85}$ | Arg, Tyr |
| $Thr^{86}$ | Ala, Asp, Glu, Gly, Ser |
| $Glu^{93}$ | Asp |
| $Lys^{102}$ | Gln, Glu |
| $Lys^{103}$ | Glu, Gln |
| $Glu^{104}$ | Met |
| $Cys^{106}$ | Ser, Ala, Met, Asn |
| $Pro^{107}$ | Ala, Asn, Gly |
| $Tyr^{108}$ | Ala, Phe, Ser |
| $Leu^{111}$ | Ala, Met, Ser |
| $Thr^{114}$ | Ala, Arg, Lys, Ser |
| $Val^{123}$ | Ile, Leu |
| $Asn^{127}$ | Asp, Glu, Lys |
| $Tyr^{130}$ | Phe |
| $Gly^{142}$ | Ala, Ser |
| $Ser^{143}$ | Ala, Glu, Lys |
| $Phe^{146}$ | Tyr, Ser, Met |
| $Leu^{152}$ | Ala, Ile, Met, Phe |
| $Asn^{159}$ | Ala, Asp, Gln Gly, Glu, Ile, Lys, Met |
| $Gly^{160}$ | Ala, His, Ser, Tyr |
| $Phe^{167}$ | Ala, Ser, Tyr |
| $Gln^{170}$ | Arg, Glu, Ser, Thr |
| $Arg^{174}$ | Gly, Ala, Ser |
| $Tyr^{177}$ | Phe, Leu |
| $Gly^{182}$ | Ala, Asp, Glu, Ser |
| $Arg^{187}$ | Ala, Glu, Gly, Ser |
| $Arg^{188}$ | Gln |
| $Lys^{195}$ | Glu, Gln |
| $Asn^{196}$ | Ala, Arg, Asp, Gln, Glu, Gly, Lys |
| $Thr^{197}$ | Ala, Arg, Asp, Lys, Glu, Gly |
| $Ser^{198}$ | Ala, Asp, Glu, Gly, Thr |
| $Val^{206}$ | Ala, Ile, Leu, Val |
| $His^{207}$ | Leu, Ser, Thr, Tyr |

It will be appreciated by those skilled in the art that many combinations of deletions, insertions and substitutions can be made, provided that the final KGF-2 protein(s) are biologically active. A variant(s) of KGF-2 may be rapidly screened to assess its physical properties. For example, the level of biological activity (e.g., receptor binding and/or affinity, mitogenic, cell proliferative and/or in vivo activity) may be tested using a variety of assays. One such assay includes a mitogenic assay to test the ability of a protein to stimulate DNA synthesis (Rubin et al. (1989), supra, the disclosure of which is hereby incorporated by reference). Another such assay includes a cell proliferative assay to test the ability of a protein to stimulate cell proliferation (Falco et al. (1988), *Oncogene*, 2:573–578, the disclosure of which is hereby incorporated by reference).

Polypeptide Derivatives

Chemically-modified derivatives of KGF-2 protein(s) in which the polypeptide is linked to a polymer in order to modify properties (referred herein as "derivatives"), are included within the scope of the present invention. Chemically-modified derivatives of KGF-2 protein(s) may be prepared by one skilled in the art given the disclosures herein. Conjugates may be prepared using glycosylated, non-glycosylated or de-glycosylated KGF-2 protein(s). Typically, non-glycosylated KGF-2 protein(s) will be used.

Suitable chemical moieties for derivatization include water soluble polymers. Water soluble polymers are desirable because the protein to which each is attached will not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically and, if so, the therapeutic profile (e.g., the duration of sustained release; resistance to proteolysis, the effects, if any, on dosage, biological activity; the ease in handling; the degree or lack of antigenicity and other known effects of a water soluble polymer on a therapeutic protein).

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol, (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone)polyethylene glycol, polypropylene glycol homopolymers (PPG) and other polyalkylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof. As used herein, polyethylene glycol is meant to encompass any of the forms that have been used to derivatize other proteins, such as mono-(C1–C10) alkoxy- or aryloxy-polyethylene glycol. Polyethylene glycol propionaldehyde may have advantages in manufacturing due to its stability in water.

The water soluble polymers each may be of any molecular weight and may be branched or unbranched. Generally, the higher the molecular weight or the more branches, the higher the polymer:protein ratio. The water soluble polymers each typically have an average molecular weight of between about 2 kDa to about 100 kDa (the term "about" indicating that in preparations of a water soluble polymer, some molecules will weigh more, some less, than the stated molecular weight). The average molecular weight of each water soluble polymer preferably is between about 5 kDa and about 40 kDa, more preferably between about 10 kDa and about 35 kDa and most preferably between about 15 kDa and about 30 kDa.

There are a number of attachment methods available to those skilled in the art, including acylation reactions or alkylation reactions (preferably to generate an N-terminal chemically modified protein) with a reactive water soluble molecule. See, for example, EP 0 401 384, the disclosure of which is hereby incorporated by reference; see also, Malik et al. (1992), *Exp. Hematol.*, 20:1028–1035; Francis (1992), *Focus on Growth Factors*, 3(2):4–10, published by Mediscript, Mountain Court, Friern Barnet Lane, London N20 OLD, UK; EP 0 154 316; EP 0 401 384; WO 92/16221; WO 95/34326; WO 95/13312; WO 96/11953; PCT International Application No. US96/19459; and the other publications cited herein that relate to pegylation, the disclosures of which are hereby incorporated by reference.

A specific embodiment of the present invention is an unbranched monomethoxy-polyethylene glycol aldehyde molecule having an average molecular weight of about 20 kDa conjugated via reductive alkylation to the N-terminus of a KGF-2 protein(s).

Polyvalent Forms

Polyvalent forms, i.e., molecules comprising more than one active moiety, may be constructed. In one embodiment, the molecule may possess multiple KGF-2 protein(s). Additionally, the molecule may possess at least one KGF-2 protein(s) and, depending upon the desired characteristic of polyvalent form, at least one other molecule.

In one embodiment, KGF-2 protein(s) may be chemically coupled. For example, KGF-2 protein(s) may be chemically coupled to a divalent water soluble molecule via the pegylation technology described above. Additionally, KGF-2 protein(s) may be chemically coupled to biotin, and the biotin/KGF-2 protein(s) which are conjugated are then allowed to bind to avidin, resulting in tetravalent avidin/biotin/KGF-2 protein(s). KGF-2 protein(s) may also be covalently coupled to dinitrophenol (DNP) or trinitrophenol (TNP) and the resulting conjugates precipitated with anti-DNP or anti-TNP-IgM to form decameric conjugates.

In yet another embodiment, a recombinant fusion protein may also be produced having KGF-2 protein(s) wherein each recombinant chimeric molecule has a KGF-2 protein(s) sequence, as described above, substituted for the variable domains of either or both of the immunoglobulin molecule heavy and light chains and having all or parts of the constant domains, but at least one constant domain, of the heavy or light chain of human immunoglobulin. For example, each such chimeric KGF-2 protein(s)/IgG1 fusion protein may be produced from two chimeric genes: KGF-2 protein(s)/human kappa light chain chimera (KGF-2 protein(s)/Ck) and KGF-2 protein(s)/human gamma-1 heavy chain chimera (KGF-2 protein(s)/Cg-1). Following transcription and translation of the two chimeric genes, as described below, the gene products may be assembled into a single chimeric molecule having a KGF-2 protein(s) displayed bivalently. Additional details relating to the construction of such chimeric molecules are disclosed in U.S. Pat. No. 5,116,964, PCT Publication No. WO 89/09622, PCT Publication No. WO 91/16437 and EP 315062, the disclosures of which are hereby incorporated by reference.

In yet a further embodiment, recombinant fusion proteins may also be produced wherein each recombinant chimeric molecule has at least one KGF-2 protein(s), as described above, and at least a portion of the region 186–401 of osteoprotegerin (OPG), as described in European Patent Application No. 96309363.8.

The production of KGF-2 protein(s) are described in further detail below. Such proteins may be prepared, for example, by recombinant techniques or by in vitro chemical synthesis of the desired KGF-2 protein(s).

Polynucleotides

Based upon the present description and using the universal codon table, one of ordinary skill in the art can readily determine all of the nucleic acid sequence which encodes an amino acid sequence of a KGF-2 protein(s).

Recombinant expression techniques conducted in accordance with the descriptions set forth below may be followed to produce these polynucleotides to express the encoded proteins. For example, by inserting a nucleic acid sequence which encodes a KGF-2 protein(s) into an appropriate vector, one skilled in the art can readily produce large quantities of the desired nucleotide sequence. The sequences can then be used to generate detection probes or amplification primers. Alternatively, a polynucleotide encoding a KGF-2 protein(s) can be inserted into an expression vector. By introducing the expression vector into an appropriate host, the desired KGF-2 protein(s) may be produced in large amounts.

As further described herein, there are numerous host/vector systems available for the propagation of desired nucleic acid sequences and/or the production of KGF-2 protein(s). These include, but are not limited to, plasmid, viral, and insertional vectors, and prokaryotic and eukaryotic hosts. One skilled in the art can adapt a host/vector system which is capable of propagating or expressing heterologous DNA to produce or express the sequences of the present invention.

Furthermore, it will be appreciated by those skilled in the art that, in view of the present disclosure, the nucleic acid sequences include the nucleic acids 109 to 624 of SEQ ID NO:1, as well as degenerate nucleic acid sequences thereof, nucleic acid sequences which encode variant(s) of mature KGF-2 and those nucleic acid sequences which hybridize (under hybridization conditions disclosed in the cDNA library screening section below, or equivalent conditions or more stringent conditions) to complements of nucleic acids 109 to 624 of SEQ ID NO:1.

Also provided by the present invention are recombinant DNA constructs involving vector DNA together with the DNA sequences encoding KGF-2 protein(s). In each such DNA construct, the nucleic acid sequence encoding a KGF-2 protein(s) (with or without signal peptides) is in operative association with a suitable expression control or regulatory sequence capable of directing the replication and/or expression of the KGF-2 protein(s) in a selected host.

Preparation of Polynucleotides

A nucleic acid sequence encoding a KGF-2 protein(s) can readily be obtained in a variety of ways including, without limitation, chemical synthesis, cDNA or genomic library screening, expression library screening, and/or PCR amplification of cDNA. These methods and others which are useful for isolating such nucleic acid sequences are set forth in Sambrook et al. (1989), *Molecular Cloning: A Laboratory Manual*, Cold Spring Harbor Laboratory Press, Cold Spring Harbor, N.Y.;

by Ausubel et al. (1994), eds *Current Protocols in Molecular Biology*, Current Protocols Press; and by Berger and Kimmel (1987), *Methods in Enzymology: Guide to Molecular Cloning Techniques*, Vol. 152, Academic Press, Inc., San Diego, Calif., the disclosures of which are hereby incorporated by reference.

Chemical synthesis of nucleic acid sequences which encode desired proteins can be accomplished using methods well known in the art, such as those set forth by Engels et al. (1989), *Angew. Chem. Intl. Ed.*, 28:716–734 and Wells et al. (1985), *Gene*, 34:315, the disclosures of which are hereby incorporated by reference. These methods include, inter alia, the phosphotriester, phosphoramidite and H-phosphonate methods of nucleic acid sequence synthesis. Large nucleic acid sequences, for example those larger than about 100 nucleotides in length, can be synthesized as several fragments. The fragments can then be ligated together to form a suitable nucleic acid sequence. A preferred method is polymer-supported synthesis using standard phosphoramidite chemistry.

Alternatively, a suitable nucleic acid sequence may be obtained by screening an appropriate cDNA library (i.e., a library prepared from one or more tissue sources believed to express the protein) or a genomic library (a library prepared from total genomic DNA). The source of the cDNA library is typically a tissue from any species that is believed to express a desired protein in reasonable quantities. The source of the genomic library may be any tissue or tissues from any mammalian or other species believed to harbor a gene encoding a KGF-2 protein(s).

Hybridization mediums can be screened for the presence of a DNA encoding a KGF-2 protein(s) using one or more nucleic acid probes (oligonucleotides, cDNA or genomic DNA fragments that possess an acceptable level of homology to the cDNA or gene to be cloned) that will hybridize selectively with cDNA(s) or gene(s) present in the library. The probes typically used for such screening encode a small region of DNA sequence from the same or a similar species as the species from which the library is prepared. Alternatively, the probes may be degenerate, as discussed herein.

Hybridization is typically accomplished by annealing the oligonucleotide probe or cDNA to the clones under conditions of stringency that prevent non-specific binding but permit binding of those clones that have a significant level of homology with the probe or primer. Typical hybridization and washing stringency conditions depend in part on the size (i.e., number of nucleotides in length) of the cDNA or oligonucleotide probe and whether the probe is degenerate. The probability of identifying a clone is also considered in designing the hybridization medium (e.g., whether a cDNA or genomic library is being screened).

Where a DNA fragment (such as cDNA) is used as a probe, typical hybridization conditions include those as set forth in Ausubel et al. (1994), eds., supra. After hybridization, the hybridization medium is washed at a suitable stringency, depending on several factors such as probe size, expected homology of probe to clone, the hybridization medium being screened, the number of clones being screened, and the like. Exemplary stringent hybridization conditions are hybridization in 4×SSC at 62–67° C., followed by washing in 0.1×SSC at 62–67° C. for approximately an hour. Alternatively, exemplary stringent hybridization conditions are hybridization in 45–55% formamide, 4×SSC at 40–45° C. Also included are DNA sequences which hybridize to the nucleic acid sequences set forth in FIG. 1 under relaxed hybridization conditions and which encode KGF-2 protein(s). Examples of such relaxed stringency hybridization conditions are 4×SSC at 45–55° C. or hybridization with 30–40% formamide at 40–45° C. See Maniatis et al. (1982), *Molecular Cloning* (A Laboratory Manual), Cold Spring Harbor Laboratory, pages 387 to 389.

There are also exemplary protocols for stringent washing conditions where oligonucleotide probes are used to screen hybridization mediums. For example, a first protocol uses 6×SSC with 0.05 percent sodium pyrophosphate at a temperature of between about 35° C. and 63° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonium chloride (TMAC) for washing. One such stringent washing solution is 3 M TMAC, 50 mM Tris-HCl, pH 8.0 and 0.2% SDS.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA (oligonucleotides) encoding a KGF-2 protein(s), are then added to the cDNA along with a polymerase such as Taq polymerase, and the polymerase amplifies the cDNA region between the two primers.

The oligonucleotide sequences selected as probes or primers should be of adequate length and sufficiently unambiguous so as to minimize the amount of non-specific binding that may occur during screening or PCR amplification. The actual sequence of the probes or primers is usually based on conserved or highly homologous sequences or regions. Optionally, the probes or primers can be fully or partially degenerate, i.e., can contain a mixture of probes/primers, all encoding the same amino acid sequence but using different codons to do so. An alternative to preparing degenerate probes is to place an inosine in some or all of those codon positions that vary by species. The oligonucleotide probes or primers may be prepared by chemical synthesis methods for DNA, as described above.

Vectors

DNA encoding a KGF-2 protein(s) may be inserted into vectors for further cloning (amplification of the DNA) or for expression. Suitable vectors are commercially available, or the vector may be specifically constructed. The selection or construction of an appropriate vector will depend on (1) whether it is to be used for DNA amplification or for DNA expression, (2) the size of the DNA to be inserted into the vector, and (3) the intended host cell to be transformed with the vector.

The vectors each involve a nucleic acid sequence which encodes a desired protein operatively linked to one or more of the following expression. control or regulatory sequences capable of directing, controlling or otherwise affecting the expression of a desired protein by a selected host cell. Each vector contains various components, depending on its function (amplification of DNA or expression of DNA) and its compatibility with the intended host cell. The vector components generally include, but are not limited to, one or more of the following: a signal sequence, an origin of replication, one or more selection or marker genes, promoters, enhancer elements, a transcription, termination sequence and the like. These components may be obtained from natural sources or be synthesized by known procedures.

Examples of suitable prokaryotic cloning vectors include bacteriophages, such as lambda derivatives, or plasmids from *E. coli* (e.g. pBR322, col E1, pUC, the F-factor and Bluescript® plasmid derivatives (Stratagene, LaJolla, Calif.)). Other appropriate expression vectors, of which numerous types are known in the art for the host cells described below, can also be used for this purpose.

Signal Sequence

The nucleic acid encoding a signal sequence may be inserted 5' of the sequence encoding a desired protein, e.g, it may be a component of a vector or it may be a part of a nucleic acid encoding a desired protein. The nucleic acid encoding the native signal sequence of KGF-2 protein(s) is known (WO 96/25422).

Origin of Replication

Expression and cloning vectors each generally include a nucleic acid sequence that enables the vector to replicate in one or more selected host cells. In a cloning vector, this sequence is typically one that enables the vector to replicate independently of the host chromosomal DNA and includes origins of replication or autonomously replicating sequences. Such sequences are well known. The origin of replication from the plasmid pBR322 is suitable for most Gram-negative bacteria, and various origins (e.g., SV40, polyoma, adenovirus, VSV or BPV) are useful for cloning vectors in mammalian cells. Generally, the origin of replication is not needed for mammalian expression vectors (for example, the SV40 origin is often used only because it contains the early promoter).

Selection Gene

The expression and cloning vectors each typically contain a selection gene. This gene encodes a "marker" protein necessary for the survival or growth of the transformed host cells when grown in a selective culture medium. Host cells that are not transformed with the vector will not contain the selection gene and, therefore, they will not survive in the culture medium. Typical selection genes encode proteins that (a) confer resistance to antibiotics or other toxins, e.g., ampicillin, neomycin, methotrexate or tetracycline; (b) complement auxotrophic deficiencies; or (c) supply critical nutrients not available from the culture medium.

Other selection genes may be used to amplify the genes to be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes the desired protein. As a result, increased quantities of the desired protein are synthesized from the amplified DNA.

For example, cells transformed with the DHFR selection gene are first identified by culturing all of the transformants in a culture medium that contains methotrexate, a competitive antagonist of DHFR. An appropriate host cell when wild-type DHFR is used is the Chinese hamster ovary cell line deficient in DHFR activity (Urlaub and Chasin (1980), *Proc. Natl. Acad. Sci., USA*, 77(7):4216–4220, the disclosure of which is hereby incorporated by reference). The transformed cells are then exposed to increased levels of methotrexate. This leads to the synthesis of multiple copies of the DHFR gene and, concomitantly, multiple copies of other DNA present in the expression vector, such as the DNA encoding the desired protein.

Promoter

Expression and cloning vectors each will typically contain a promoter that is recognized by the host organism and is operably linked to a nucleic acid sequence encoding the desired protein. A promoter is an untranslated sequence located upstream (5') to the start codon of a structural gene (generally within about 100 to 1000 bp) that controls the transcription and translation of a particular nucleic acid sequence. A promoter may be conventionally grouped into one of two classes, inducible promoters and constitutive promoters. An inducible promoter initiates increased levels of transcription from DNA under its control in response to some change in culture conditions, such as the presence or absence of a nutrient or a change in temperature. A large number of promoters, recognized by a variety of potential host cells, are well known. A promoter may be operably linked to DNA encoding the desired protein by removing the promoter from the source DNA by restriction enzyme digestion and inserting the desired promoter sequence. The native KGF-2 promoter sequence may be used to direct amplification and/or expression of DNA encoding a desired protein. A heterologous promoter is preferred, however, if it permits greater transcription and higher yields of the expressed protein as compared to the native promoter and if it is compatible with the host cell system that has been selected for use. For example, any one of the native promoter sequences of other FGF family members may be used to direct amplification and/or expression of the DNA encoding a desired protein.

Promoters suitable for use with prokaryotic hosts include the beta-lactamase and lactose promoter systems; alkaline phosphatase, a tryptophan (trp) promoter system; a bacterial luminescence (luxR) gene system; and hybrid promoters such as the tac promoter. Other known bacterial promoters are also suitable. Their nucleotide sequences have been published, thereby enabling one skilled in the art to ligate them to the desired DNA sequence(s) using linkers or adaptors as needed to supply any required restriction sites.

Suitable promoting sequences for use with yeast hosts are also well known in the art. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and, most preferably, Simian Virus 40 (SV40). Other suitable mammalian promoters include heterologous mammalian promoters, e.g., heat-shock promoters and the actin promoter.

Enhancer Element

The expression and cloning vectors each will typically contain an enhancer sequence to increase the transcription by higher eukaryotes of a DNA sequence encoding a desired protein. Enhancers are cis-acting elements of DNA, usually from about 10–300 bp in length, that act on the promoter to increase its transcription.

Enhancers are relatively orientation and position independent. They have been found 5' and 3' to the transcription unit. Yeast enhancers are advantageously used with yeast promoters. Several enhancer sequences available from mammalian genes are known (e.g., globin, elastase, albumin, alpha-feto-protein and insulin). Additionally, viral enhancers such as the SV40 enhancer, the cytomegalovirus early promoter enhancer, the polyoma enhancer and adenovirus enhancers are exemplary enhancing elements for the activation of eukaryotic promoters. While an enhancer may be spliced into a vector at a position 5' or 3' to a DNA encoding a desired protein, it is typically located at a site 5' from the promoter.

Transcription Termination

Expression vectors used in eukaryotic host cells each will typically contain a sequence necessary for the termination of transcription and for stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding a desired protein.

The construction of a suitable vector containing one or more of the above-listed components (together with the desired coding sequence) is accomplished by standard ligation techniques. Isolated plasmids or DNA fragments are cleaved, tailored and religated in the desired order to generate the required vector. To confirm that the correct sequence has been constructed, the ligation mixture may be used to transform $E.$ $coli$, and successful transformants may be selected by known techniques as described above. Quantities of the vector from the transformants are then prepared, analyzed by restriction endonuclease digestion, and/or sequenced to confirm the presence of the desired construct.

A vector that provides for the transient expression of DNA encoding a desired protein in mammalian cells may also be used. In general, transient expression involves the use of an expression vector that is able to replicate efficiently in a host cell, such that the host cell accumulates many copies of the expression vector and, in turn, synthesizes high levels of the desired protein encoded by the expression vector. Each transient expression systems, comprising a suitable expression vector and a host cell, allows for the convenient positive identification of proteins encoded by cloned DNAs, as well as for the rapid screening of such proteins for desired biological or physiological properties.

Host Cells

Any of a variety of recombinant host cells, each of which contains a nucleic acid sequence for use in expressing a desired protein, is also provided by the present invention. Exemplary prokaryotic and eukaryotic host cells include bacterial, mammalian, fungal, insect, yeast or plant cells.

Prokaryotic host cells include but are not limited to eubacteria such as Gram-negative or Gram-positive organisms (e.g., $E.$ $coli$ (HB101, DH5a, DH10 and MC1061); Bacilli such as $B.$ $subtilis$; Pseudomonas species, such as $P.$ $aeruginosa$; Streptomyces spp.; $Salmonella$ $typhimurium$; or $Serratia$ $marcescans$. As a specific embodiment, a KGF-2 protein(s) may be expressed in $E.$ $coli$.

In addition to prokaryotic host cells, a KGF protein(s) may be expressed in glycosylated form by any one of a number of suitable host cells derived from multicellular organisms. Such host cells are capable of complex processing and glycosylation activities. In principle, any higher eukaryotic cell culture might be used, whether such culture involves vertebrate or invertebrate cells, including plant and insect cells.

Eukaryotic microbes such as filamentous fungi or yeast may be suitable hosts for the expression of a KGF-2 protein(s). $Saccharomyces$ $cerevisiae$, or common baker's yeast, is the most commonly used among lower eukaryotic host microorganisms, but a number of other genera, species and strains are well known and commonly available.

Vertebrate cells may be used, as the propagation of vertebrate cells in culture (tissue culture) is a well-known procedure. Examples of useful mammalian host cell lines include but are not limited to monkey kidney CV1 line transformed by SV40 (COS-7), human embryonic kidney line (293 cells or 293 cells subcloned for growth in suspension culture), baby hamster kidney cells and Chinese hamster ovary cells. Other suitable mammalian cell lines include but are not limited to HeLa, mouse L-929 cells, 3T3 lines derived from Swiss, Balb-c or NIH mice, and BHK or HaK hamster cell lines. As a specific embodiment, a KGF-2 protein(s) may be expressed in COS cells or in baculovirus cells.

A host cell may be transfected and preferably transformed with a desired nucleic acid under appropriate conditions permitting expression of the nucleic acid. The selection of suitable host cells and methods for transformation, culture, amplification, screening and product production and purification are well known in the art (Gething and Sambrook (1981), $Nature$, 293:620–625 or, alternatively, Kaufman et al. (1985), $Mol.$ $Cell.$ $Biol.$, 5(7):1750–1759, or U.S. Pat. No. 4,419,446, the disclosures of which are hereby incorporated by reference). For example, for mammalian cells without cell walls, the calcium phosphate precipitation method may be used. Electroporation, microinjection and other known techniques may also be used.

It is also possible that a desired protein may be produced by homologous recombination or with recombinant production methods utilizing control elements introduced into cells already containing MA encoding a KGF-2 protein(s). Homologous recombination is a technique originally developed for targeting genes to induce or correct mutations in transcriptionally active genes (Kucherlapati (1989), $Prog.$ $in$ $Nucl.$ $Acid$ $Res.$ $and$ $Mol.$ $Biol.$, 36:301, the disclosure of which is hereby incorporated by reference). The basic technique was developed as a method for introducing specific mutations into specific regions of the mammalian genome (Thomas et al. (1986), $Cell$, 44:419–428; Thomas and Capecchi (1987), $Cell$, 51:503–512 and Doetschman et al. (1988), $Proc.$ $Natl.$ $Acad.$ $Sci.$, 85:8583–8587, the disclosures of which are hereby incorporated by reference) or to correct specific mutations within defective genes (Doetschman et al. (1987), $Nature$, 330:576–578, the disclosure of which is hereby incorporated by reference). Exemplary techniques are described in U.S. Pat. No. 5,272,071; WO 92/01069; WO 93/03183; WO 94/12650 and WO 94/31560, the disclosures of which are hereby incorporated by reference.

Culturing the Host Cells

The method for culturing each of the one or more recombinant host cells for production of a desired protein will vary depending upon many factors and considerations; the optimum production procedure for a given situation will be apparent to those skilled in the art through minimal experimentation. Such recombinant host cells are cultured in suitable medium and the expressed protein is then optionally recovered, isolated and purified from the culture medium (or from the cell, if expressed intracellularly) by appropriate means known to those skilled in the art.

Specifically, each of the recombinant cells used to produce a desired protein may be cultured in media suitable for inducing promoters, selecting suitable recombinant host cells or amplifying the gene encoding the desired protein. The media may be supplemented as necessary with hormones and/or other growth factors (such as insulin, transferrin or epidermal growth factor), salts (such as sodium chloride, calcium, magnesium and phosphate), buffers (such as HEPES), nucleosides (such as adenosine and thymidine), antibiotics (such as gentamicin), trace elements (defined as inorganic compounds usually present at final concentrations in the micromolar range), and glucose or another energy source. Other supplements may also be included, at appropriate concentrations, as will be appreciated by those skilled in the art. Suitable culture conditions, such as temperature, pH and the like, are also well known to those skilled in the art for use with the selected host cells.

The resulting expression product may then be purified to near homogeneity using procedures known in the art. Exemplary purification techniques are taught in published PCT Application Nos. WO 90/08771 and WO 96/11952, the disclosures of which are hereby incorporated by reference.

Uses

Variant(s) of KGF-2 described herein, and chemically-modified derivatives of KGF-2 and variant(s) of KGF-2 protein (collectively, "KGF-2 protein product(s)") may be used as research reagents and as therapeutic and diagnostic agents. Thus, a KGF-2 protein product(s) may be used in in vitro and/or in vivo diagnostic assays to quantify the amount of KGF-2 in a tissue or organ sample.

For example, a KGF-2 protein product(s) can be used for identification of the receptor(s) for a KGF-2 protein(s) in various body fluids and tissue samples using techniques known in the art (WO 90/08771).

This invention also contemplates the use of a KGF-2 protein product(s) in the generation of antibodies made against the KGF-2 protein product(s), including native KGF-2. One of ordinary skill in the art can use well-known, published procedures to obtain monoclonal and polyclonal antibodies or recombinant antibodies. Such antibodies may then be used to purify and characterize KGF-2 protein product(s), including native KGF-2.

Pharmaceutical Compositions

The present invention encompasses pharmaceutical preparations each containing therapeutically- or prophylatically-effective amounts of a KGF-2 protein product(s).

Pharmaceutical compositions each will generally include a therapeutically-effective or prophylatically-effective amount of a KGF-2 protein product(s) in admixture with a vehicle. The vehicle preferably includes one or more pharmaceutically and physiologically acceptable formulation materials in admixture with the KGF-2 protein product(s).

The primary solvent in a vehicle may be either aqueous or non-aqueous in nature. In addition, the vehicle may contain other pharmaceutically acceptable excipients for modifying or maintaining the pH (e.g., buffers such as citrates, phosphates, and amino acids such as glycine); osmolarity (e.g., mannitol and sodium chloride); viscosity; clarity; color; sterility; stability (e.g., sucrose and sorbitol); odor of the formulation; rate of dissolution (e.g., solubilizers or solubilizing agents such as alcohols, polyethylene glycols and sodium chloride); rate of release; as well as bulking agents for lyophilized formulation (e.g., mannitol and glycine); surfactants (e.g., polysorbate 20, polysorbate 80, triton, and pluronics); antioxidants (e.g., sodium sulfite and sodium hydrogen-sulfite); preservatives (e.g., benzoic acid and salicylic acid); flavoring and diluting agents; emulsifying agents; suspending agents; solvents; fillers; delivery vehicles; diluents and/or pharmaceutical adjuvants. Other effective administration forms such as parenteral slow-release formulations, inhalant mists, orally-active formulations, or suppositories are also envisioned.

The composition may also involve particulate preparations of polymeric compounds such as bulk erosion polymers (e.g., poly(lactic-co-glycolic acid) (PLGA) copolymers, PLGA polymer blends, block copolymers of PEG, and lactic and glycolic acid, poly(cyanoacrylates)); surface erosion polymers (e.g., poly(anhydrides) and poly (ortho esters)); hydrogel esters (e.g., pluronic polyols, poly (vinyl alcohol), poly(vinylpyrrolidone), maleic anhydride-alkyl vinyl ether copolymers, cellulose, hyaluronic acid derivatives, alginate, collagen, gelatin, albumin, and starches and dextrans) and composition systems thereof; or preparations of liposomes or microspheres. Such compositions may influence the physical state, stability, rate of in vivo release, and rate of in vivo clearance of the present proteins and derivatives. The optimal pharmaceutical formulation for a desired protein will be determined by one skilled in the art depending upon the route of administration and desired dosage. Exemplary pharmaceutical compositions are disclosed in *Remington's Pharmaceutical Sciences*, 18th Ed. (1990), Mack Publishing Co., Easton, Pa. 18042, pages 1435–1712; Gombotz and Pettit (1995), *Bioconjugate Chem.*, 6:332–351; Leone-Bay, et al. (1995), *Journal of Medicinal Chemistry*, 38:4263–4269; Haas, et al. (1995), *Clinical Immunology and Immunopathology*, 76(1):93; WO 94/06457; WO 94/21275; FR 2706772 and WO 94/21235, the disclosures of which are incorporated herein by reference.

Specific sustained release compositions are available from the a variety of suppliers including Depotech Corp. (Depofoam™, a multivesicular liposome); Alkermes, Inc. (ProLease™, a PLGA microsphere). As used herein, hyaluronan is intended to include hyaluronan, hyaluronic acid, salts thereof (such as sodium hyaluronate), esters, ethers, enzymatic derivatives and cross-linked gels of hyaluronic acid, and chemically modified derivatives of hyaluronic acid (such as hylan). Exemplary forms of hyaluronan are disclosed in U.S. Pat. Nos. 4,582,865, 4,605,691, 4,636,524, 4,713,448, 4,716,154, 4,716,224, 4,772,419, 4,851,521, 4,957,774, 4,863,907, 5,128,326, 5,202,431, 5,336,767, 5,356,883; European Patent Application Nos. 0 507 604 A2 and 0 718 312 A2; and WO 96/05845, the disclosures of which are hereby incorporated by reference. Suppliers of hyaluronan include Biomatrix, Inc. Ridgefield, N.J.; Fidia S.p.A., Abano Terme, Italy; Kaken Pharmaceutical Co., Ltd., Tokyo, Japan; Pharmacia AB, Stockholm, Sweden; Genzyme Corporation, Cambridge, Mass.; Pronova Biopolymer, Inc. Portsmouth, N.H.; Calbiochem-Novabiochem AB, Lautelfingen, Switzerland; Intergen Company, Purchase, N.Y. and Kyowa Hakko Kogyo Co., Ltd., Tokyo, Japan.

For treatment and/or prevention of oral indications, a liquid solution or suspension can be used in a manner similar to a mouthwash, where the liquid is swished around in the mouth so as to maximize treatment of lesions (U.S. Pat. No. 5,102,870, the teachings of which are incorporated by reference). Longer contact with the mucosal surface can be attained by selecting a suitable vehicle which is capable of coating mucosa. Typical examples are pectin containing formulations such as Orabase Registered™ (Colgate-Hoyt Laboratories, Norwood, Mass.), sucralfate suspensions, Kaopectate and Milk of Magnesia. The formulation can also be a spreadable cream, gel, lotion or ointment having a pharmaceutically acceptable non-toxic vehicle or carrier. KGF-2 protein product(s) can also be incorporated into a slow dissolving lozenge or troche, a chewing gum base, or a buccal or slow delivery prosthesis hooked onto a back molar, for example. Therapeutic agents such as analgesics and anesthetics can be administered to alleviate pain and such as anti-infectictives, anti-bacterials, anti-fungals and antiseptics can be administered to prevent and/or treat secondary infection of the lesions.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Kits included within the scope of this invention are single and multi-chambered pre-filled syringes; exemplary pre-filled syringes (e.g., liquid syringes, and lyosyringes such as Lyo-Ject®, a dual-chamber pre-filled lyosyringe) are available from Vetter GmbH, Ravensburg, Germany.

It should be noted that KGF-2 protein product(s) formulations described herein may be used for veterinary as well as human applications and that the term "patient" should not be construed in a limiting manner.

The frequency of dosing the KGF-2 protein product(s) to a patient will depend on the disease and the condition of the patient, as well as the pharmacokinetic parameters of KGF-2 protein product(s) as formulated, and the route of administration. The KGF-2 protein product(s) may be administered once, administered daily, or administered with an initial bolus dose followed by a continuous dose or sustained delivery. It is also contemplated that other modes of a continuous or near-continuous dosing may be practiced. For example, chemical derivatization may result in sustained release forms of the protein which have the effect of a continuous presence in the bloodstream, in predictable amounts, based on a determined dosage regimen.

A patient in need of stimulation (including cytoprotection, proliferation and/or differentiation) of epithelial cells may be administered an effective amount of a KGF-2 protein product(s) to elicit the desired response in the patient and will, thus, generally be determined by the attending physician. The dosage regimen involved in a method of preventing or treating a specific condition will be determined by the attending physician, considering various factors which modify the action of drugs, e.g., the age, condition, body weight, sex and diet of the patient, the severity of any infection, the time of administration and other clinical factors. Appropriate dosages may be ascertained through use of established assays for determining dosages utilized in conjunction with appropriate dose-response data. Typical dosages will range from 0.001 mg/kg body weight to 500 mg/kg body weight, preferably up to 200 mg/kg body weight, more preferably 100 mg/kg body weight.

The KGF-2 protein product(s) may be administered via topical, enteral or parenteral administration including, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion. The KGF-2 protein product(s) may be administered via oral administration or administered through mucus membranes, that is, intranasally, sublingually, buccally or rectally for systemic delivery. The KGF-2 protein product(s) may be used once or administered repeatedly, depending on the disease and the condition of the patient. In some cases, the KGF-2 protein product(s) may be administered as an adjunct to other therapy and also with other pharmaceutical preparations In another embodiment, cell therapy (e.g., implantation of cells producing KGF-2 protein(s) is also contemplated. This embodiment of the present invention may include implanting into patients cells which are capable of synthesizing and secreting a biologically-active form of KGF-2 protein(s). Such cells producing KGF-2 protein(s) may be cells which do not normally produce KGF-2 protein(s) but which have been modified to produce KGF-2 protein(s), or which may be cells whose ability to produce KGF-2 protein(s) have been augmented by transformation with a polynucleotide suitable for the expression and secretion of such protein. In order to minimize a potential immunological reaction in patients being administered KGF-2 protein(s) of a foreign species, it is preferred that the cells be of the same species as the patient (e.g., human) or that the cells may be encapsulated with material that provides a barrier against immune recognition, or that cells be placed into an immunologically-privileged anatomical location, such as in the testis, eye and central nervous system.

Human or non-human animal cells may be implanted in patients in biocompatible, semi-permeable polymeric enclosures or membranes to allow release of a KGF-2 protein(s), but prevent destruction of the cells by the patient's immune system or by other detrimental factors from the surrounding tissue. Alternatively, the patient's own cells, transformed ex vivo to produce KGF-2 protein(s), could be implanted directly into the patient without such encapsulation. The methodology for the membrane encapsulation of living cells is familiar to those of ordinary skill in the art, and the preparation of the encapsulated cells and their implantation in patients may be accomplished with known techniques (U.S. Pat. Nos. 4,892,538; 5,011,472; and 5,106,627, the disclosures of which are hereby incorporated by reference).

In yet another embodiment, in vivo gene therapy is also envisioned, wherein a nucleic acid sequence encoding a KGF-2 protein(s) is introduced directly into a patient. Efficient and long lasting gene transfer to hepatocytes is required for effective gene therapy for local expression of the protein to prevent and/or treat liver diseases and/or for secretion of the protein to prevent and/or treat diseases in other organs or tissues.

The DNA construct may be directly injected into the tissue of the organ to be treated, where it can be taken up in vivo and expressed, provided that the DNA is operable linked to a promoter that is active in such tissue. The DNA construct may also additionally include vector sequence from such vectors as an adenovirus vector, a retroviral vector, papilloma virus and/or a herpes virus vector, to aid uptake in the cells. Physical transfer may be achieved in vivo by local injection of the desired nucleic acid construct or other appropriate delivery vector containing the desired nucleic acid sequence, such as liposome-mediated transfer, direct injection (naked DNA), receptor-mediated transfer (ligand-DNA complex), or microparticle bombardment (gene gun). For the in vivo regeneration of hepatocytes in the liver, the use of Moloney retroviral vectors may be especially effective (Bosch, et al. (1996), Cold Spring Harbor, Gene Therapy Meeting, Sep. 25–29, 1996; and Bosch, et al. (1996), *Journal of Clinical Investigation*, 98(12):2683–2687).

A KGF-2 protein product(s) may be applied in therapeutically- and prophylactically-effective amounts to organs or tissues specifically characterized by having damage to or clinically insufficient numbers of epithelium cells. It should be noted that a KGF-2 protein product(s) may be used for veterinary as well as human applications and that the term "patient" should not be construed in a limiting manner.

In accordance with the present invention, a KGF-2 protein product(s) may be used in vivo to induce stimulation (including cytoprotection, proliferation and/or differentiation), proliferation and/or differentiation of epithelial cells including, but not limited to, the eye, ear, gums, hair, lung, skin, pancreas (endocrine and exocrine), thymus, thyroid, urinary bladder, liver and gastrointestinal tract including cells in the oral cavity, in the esophagus, in the glandular stomach and small intestine, in the colon and the intestinal mucosa, in the rectum and in the anal canal. Indications in which a KGF-2 protein product(s) may be successfully administered include, but are not limited to: burns and other partial and full-thickness injuries in need of stimulation of adnexal structures such as hair follicles, sweat glands, and sebaceous glands; lesions caused by epidermolysis bullosa, which is a defect in adherence of the epidermis to the underlying dermis, resulting in frequent open, painful blisters which can cause severe morbidity; chemotherapy-induced alopecia and male-pattern baldness, or the progressive loss of hair in men and women; gastric and duodenal ulcers; gut toxicity in radiation- and chemotherapy-treatment regimes; erosions of the gastrointestinal tract (e.g., esophagus, stomach and intestines) include erosive gastritis, esophagitis, esophageal reflux or inflammatory bowel diseases, such as Crohn's disease (affecting primarily the small intestine) and ulcerative colitis (affecting primarily the large bowel); disorders or damage to salivary gland tissue including radiation/chemotherapy effects, autoimmune diseases such as Sjogren's Syndrome which can cause salivary gland insufficiency (sicca syndrome); insufficient production of mucus throughout the gastrointestinal tract; adult respiratory distress syndrome (ARDS), pneumonia, hyaline membrane disease (i.e., infant respiratory distress syndrome and bronchopulmonary dysplasia) in premature infants; acute or chronic lung damage or insufficiency due to inhalation injuries (including high oxygen levels), emphysema, lung damage from chemotherapeutics, ventilator trauma or other lung damaging circumstances; hepatic cirrhosis, fulminant liver failure, damage caused by acute viral hepatitis and/or toxic insults to the liver and/or bile duct disorders, and viral-mediated gene transfer to liver; corneal abrasion and/or corneal ulcerations due to chemicals, bacteria or viruses; progressive gum disease; eardrum damage; ulcerations and/or inflammations including conditions resulting from chemotherapy and/or infection; pancreatic disorders and pancreatic insufficiencies including diabetes (Type I and Type II), pancreatitis, cystic fibrosis, and as an adjunct in islet cell transplantation.

This invention thus has significant implications in terms of enabling the application of KGF-2 protein product(s) specifically characterized by the prophylactic and/or therapeutic use of KGF-2 to reduce, delay and/or block the onset of damage to or deficiencies in these particular types of cells. The following is a more specific description of diseases and medical conditions which can be treated with KGF-2 protein product(s) in accordance with the invention.

Specific uses of the KGF-2 protein products) are disclosed in patent application Ser. No. 09/284,101, filed on the same date herewith by Lacey, Ulich, Danilenko and Farrell, entitled on the Application transmittal letter as "USES OF KERATINOCYTE GROWTH FACTOR-2", the disclosure of which is hereby incorporated by reference.

KGF-2 protein product(s) are useful to increase cytoprotection, proliferation and/or differentiation of hepatocytes in order to increase liver-function. KGF-2 protein product(s) are useful to treat and/or prevent hepatic cirrhosis, fulminant liver failure, damage caused by acute viral hepatitis, toxic insults to the liver and/or bile duct disorders.

Hepatic cirrhosis, secondary to viral hepatitis and chronic alcohol ingestion, is a significant cause of morbidity and mortality. KGF-2 protein product(s) are useful to treat and/or prevent the development of cirrhosis. A standard in vivo model of hepatic cirrhosis is known (Tomaszewski et al. (1991), *J. Appl. Toxicol.*, 11:229–231, the disclosure of which is hereby incorporated by reference).

Fulminant liver failure is a life-threatening condition which occurs with end-stage cirrhosis and which is presently treatable only with liver transplantation. KGF-2 protein product(s) are useful to treat and/or prevent fulminant liver failure. Standard in vivo models of fulminant liver failure are known (Mitchell et al. (1973), *J. Pharmacol. Exp. Ther.*, 187:185–194; Thakore and Mehendale (1991), *Toxicologic Pathol.*, 19:47–58; and Havill et al. (1994), *FASEB Journal*, 8(4–5):A930, Abstract 5387, the disclosures of which are hereby incorporated by reference).

Acute viral hepatitis is frequently subclinical and self-limiting. However, in a minority of patients severe liver damage can result over several weeks. KGF-2 protein product(s) are useful in preventing and/or treating viral hepatitis. Standard in vivo models of hepatocyte proliferation are known (Housley et al. (1994), *Journal of Clinical Investigation*, 94(5):1764–1777; and Havill et al. (1994), supra, the disclosures of which are hereby incorporated by reference).

Toxic insults to the liver caused by acetaminophen, halothane, carbon tetrachloride and other toxins may be prevented and/or treated by KGF-2 protein product(s). Standard in vivo models of liver toxicity are known (Mitchell et al. (1973), supra; Thakore and Mehendale (1991), supra; and Havill et al. (1994), supra, the disclosures of which are hereby incorporated by reference).

KGF-2 protein product(s) are useful to increase cytoprotection, proliferation and/or differentiation of epithelial cells in the gastrointestinal tract (e.g., the oral cavity, esophagus, stomach, small intestine, colon, rectum and anal canal). The terms "gastrointestinal tract", as defined herein, and "gut" are art-recognized terms and are used interchangeably herein. Specifically, KGF-2 protein product(s) are useful to treat and/or prevent gastric ulcers, duodenal ulcers, inflammatory bowel disease, gut toxicity and erosions of the gastrointestinal tract.

Gastric ulcers cause significant morbidity, have a relatively high recurrence rate, and heal by scar formation on the mucosal lining. KGF-2 protein product(s) are useful to prevent degeneration of glandular mucosa and to regenerate glandular mucosa more rapidly, e.g., offering a significant therapeutic improvement in the treatment of gastric ulcers. Standard in vivo models of gastric ulcers are known (Tarnawski et al. (1991), "Indomethacin Impairs Quality of Experimental Gastric Ulcer Healing: A Quantitative Histological and Ultrastructural Analysis", In:*Mechanisms of Injury, Protection and Repair of the Upper Gastrointestinal Tract*, (eds) Garner and O'Brien, Wiley & Sons; Brodie (1968), *Gastroenterology*, 55:25; and Ohning et al. (1994),

*Gastroenterology*, 106(4 Suppl.):A624, the disclosures of which are hereby incorporated by reference).

Duodenal ulcers, like gastric ulcers, cause significant morbidity and have a relatively high recurrence rate. KGF-2 protein product(s) are useful to prevent degeneration of the mucosal lining of the duodenum and to rapidly regenerate the mucosal lining of the duodenum to heal those ulcers and decrease their recurrence. Standard in vivo models of duodenal ulcers are known (Berg et al. (1949), *Proc. Soc. Exp. Biol. Med.*, 7:374–376; Szabo and Pihan, *Chronobiol. Int.* (1987), 6:31–42; and Robert et al. (1970), *Gastroenterology*, 59:95–102, the disclosures of which are hereby incorporated by reference).

Gut toxicity is a major limiting factor associated with cancer treatment, both in radiation (abdominal, total body or local, e.g., head and neck) and chemotherapy. Of primary concern are those patients undergoing: chemotherapy for cancer such as leukemia, breast cancer or as an adjuvant to tumor removal; radiotherapy for head and neck cancer; and combined chemotherapy and radiotherapy for bone marrow transplants. The severity of damage is related to the type and dose of chemotherapeutic agent(s) and concomitant therapy such as radiotherapy.

Mucositis in portions of the gastrointestinal tract may account for significant pain and discomfort for these patients, and range in severity from redness and swelling to frank ulcerative lesions. The lesions often become secondarily infected and become much harder to heal. Standard in vivo models of radiation-induced gut toxicity are known (Withers and Elkind (1970), *Int. J. Radiat.*, 17(3):261–267, the disclosure of which is hereby incorporated by reference). Standard in vivo models of chemotherapy-induced gut toxicity are known (Farrell et al., The American Society of Hematology, 38th Annual Meeting (Orlando, Fla.), Dec. 6–8, 1996; Sonis et al. (1990), *Oral Surg. Oral Med & Oral Pathol.*, 69(4):437–443; and Moore (1985), *Cancer Chemotherapy Pharmacol.*, 15:11–15, the disclosures of which are hereby incorporated by reference).

Exemplary chemotherapeutic agents include, but are not limited to, BCNU, busulfan, carboplatin, cyclophosphamide, cisplatin, cytosine arabinoside, daunorubicin, doxorubicin, etoposide, 5-fluorouracil, gemcytabine, ifosphamide, irinotecan, melphalan, methotrexate, navelbine, topotecan, taxol and taxotere, and exemplary treatment regimes include, but are not limited to, BEAM (busulfan, etoposide, cytosine arabinoside, methotrexate); cyclophosphamide and total body irradiation; cyclophosphamide, total body irradiation and etoposide; cyclophosphamide and busulfan; and 5-fluorouracil with leucovorin or levamisole.

Treatment, pretreatment and/or post-treatment, with KGF-2 protein product(s) are useful to generate a cytoprotective effect or regeneration or both, for example, on the small intestinal mucosa, allowing increased dosages of such therapies while reducing potential fatal side effects of gut toxicity.

KGF-2 protein product(s) may preferentially be administered in the following settings. Colorectal patients routinely are administered 5-fluorouracil with leucovorin on days 1 to 5; KGF-2 protein product(s) may be administered on days −2, −1 and 0. Head and neck cancer patients routinely are administered hypofractionated radiation therapy, plus 5-fluorouracil and cisplatin over a seven week period; KGF-2 protein product(s) may be administered on days −2, −1 and 0 and thereafter once per week until the end of the radiation therapy. In lymphoma transplantation patients are frequently administered BEAM therapy for 6 days (days 1 to 6); KGF protein product(s) may be administered on days −2, −1 and 0 and as a three day post-treatment (days 7 to 9).

In specific embodiments, KGF-2 protein product(s) may be administered prophylactically and/or therapeutically to reduce, delay and/or block the onset of mucositis (due to chemotherapy and/or radiotherapy), in combination with one or more cytokines to delay and/or block the onset of cytopenia.

Typically, bone marrow, peripheral blood progenitor cells or stem cells (McNiece et al. (1989), *Blood*, 74:609–612 and Moore et al. (1979), *Blood Cells*, 5:297–311, the disclosures of which are hereby incorporated by reference) are removed from a patient prior to myelosuppressive cytoreductive therapy (chemotherapy alone or with radiation therapy) and are then readministered to the patient concurrent with or following cytoreductive therapy in order to counteract the myelosuppressive effects of such therapy.

Many different approaches have been undertaken to protect an organism from the side effects of radiation or toxic chemicals. One approach is to replace bone marrow cells before toxicity has developed. Another approach is to use progenitor cells from the peripheral blood (PBPC). These PBPC can be collected by apheresis or phlebotomy following cytokine therapy alone (G-CSF or GM-CSF), or with chemotherapy or cytokines. They can be given back fresh or cryopreserved. If desired, the cells may be CD34+ selected, Tn-cell depleted, tumor cell depleted, or the progenitor cells can be expanded (caused to multiply) by means known in the art, prior to administration. The benefits of re-infusion of autologous or allogeneic progenitors following myelosuppressive therapy have been described in the literature (Morse et al. (1992), *Ann. Clin. Lab. Sci.*, 22:221–225; Kessinger and Armitage (1991), *Blood*, 77:211–213; Kessinger et al. (1989), Blood, 74:1260–1265; Takam et al. (1989), *Blood*, 74:1245–1251 and Kessinger et al. (1988), *Blood*, 171:723–727).

As used herein, the term "cytokine" is a generic term for proteins released by one cell population which act on another cell as intercellular mediators. Examples of such cytokines are lymphokines, monokines and traditional polypeptide hormones. Included among the cytokines are insulin-like growth factors; human growth hormone; N-methionyl human growth hormone; bovine growth hormone; parathyroid hormone; thyroxine; insulin; proinsulin; relaxin; prorelaxin; glycoprotein hormones such as follicle stimulating hormone (FSH), thyroid stimulating hormone (TSH) and leutinizing hormone (LH); hemopoietic growth factor; hepatic growth factor; fibroblast growth factor; prolactin; placental lactogen; tumor necrosis factor alpha and -beta; mouse gonadotropin-associated peptide; inhibin; activin; vascular endothelial growth factor; integrin; thrombopoietin; nerve growth factors such as NGF-beta; platelet-growth factors such as TPO and MGDF; transforming growth factors (TGFs) such as TGF-alpha and TGF-beta; insulin-like growth factor-I and -II; erythropoietin; osteoinductive factors; interferons such as interferon-alpha, -beta and -gamma; colony stimulating factors (CSFs) such as macrophige-CSF (M-CSF), granulocyte-macrophage-CSF (GM-CSF), and granulocyte-CSF (G-CSF); interleukins (ILs) such as IL-1, IL-2, IL-3, IL-4, IL-5, IL-6, IL-7, IL-8, IL-9, IL-10, IL-11, IL-12, IL-13, IL-14, IL-15 and IL-16; and other polypeptide factors. The cytokines can be used alone or in combination to protect against, mitigate and/or reverse myeloid or hematopoietic toxicity associated with cytotoxic agents.

The mode of administration of KGF-2 protein product(s), as well as of the cytokine, should be coordinated and optimized. Depending upon the circumstances, an appropriate dose of KGF-2 protein product(s) can be administered prior to or subsequent to administration of the therapeutic agent(s). For example, a parameter to be considered is whether the cytokine is administered in a single dose or in multiple doses during the course of therapy. Certain cytokines are cleared rapidly from the body and will require periodic or continuous administration in order for their efficacy to be maximized. The manner of administration can differ, depending on whether a pre-treatment or post-treatment of the cytokine is given. For example, if the cytokine is given prior to the cytotoxic agent, it is preferable to administer the cytokine by intravenous bolus injection for several hours and, optionally, to repeat such administration on one or more days during and after completion of the cytotoxic therapy.

In a specific embodiment, KGF-2 protein product(s) are administered (e.g., intraveneously) at 0.1 to 500 micrograms/kg/dose, preferably up to about 200 micrograms/kg/dose, prior to (e.g., 1 to 3 days) and/or after chemotherapy or radiation therapy, and G-CSF (Neupogen™ or Lenograstim™) or GM-CSF (Sargramostim™) is administered (e.g., subcutaneously) at 5 micrograms/kg/dose for 1 to 10 days (preferably 7 to 10 days) after chemotherapy.

Erosions of the gastrointestinal tract (e.g., esophagus, stomach-and intestine) include erosive gastritis, esophagitis, esophageal reflux and inflammatory bowel diseases. Inflammatory bowel diseases, such as Crohn's disease (affecting primarily the small intestine) and ulcerative colitis (affecting primarily the large bowel), are chronic diseases of unknown etiology which result in the destruction of the mucosal surface, inflammation, scar and adhesion formation during repair, and significant morbidity to the affected individuals. KGF-2 protein product(s) are useful to regenerate the mucosal lining and decrease the recurrence of these erosions, resulting in faster healing, and may be of benefit in controlling progression of the disease. Standard in vivo models of erosion of the gastrointestinal tract are known (Geisinger et al. (1990), *Mod-Pathol.*, 3(5):619–624; Carlborg et al. (1983), *Laryngoscope*, 93(2):184–187; Carlborg et al. (1980), *Eur-Surg-Res.*, 12(4):270–282; Keshavarzian et al. (1991), *Alcohol-Clin-Exp-Res.*, 15(1):116–121; Katz et al. (1988), *Dig-Dis-Sci.*, 33(2):217–224; and Zeeh et al. (1996), *Gastroenterology*, 110(4):1077–1083, the disclosures of which are hereby incorporated by reference). Standard in vivo models of inflammatory bowel disease are well known (Morris et al. (1989), *Gastroenterology*, 96:795–803; Rachmilewitz et al. (1989), *Gastroenterology*, 97:326–327; Allgayer et al. (1989), *Gastroenterology*, 96:1290–1300; and Kim and Borstad (1992), *Scand. J. Gastroenterol*, 27(7):529–537, the disclosures of which are hereby incorporated by reference).

Animal studies have established the relationship between total parenteral nutrition (TPN) and intestinal mucosal atrophy (Buchman et al. (1995), *Journal of Parenteral and Enteral Nutrition*, 19:453–460). The decrease in intestinal villus height is attributed to the lack of growth stimulus provided through oral intake of nutrients. This is reflected in a reduction in the labeling index, a measure of growth. Decreases in villus height are also correlated with decreases in specific activities of enzymes involved in nutrient absorption. KGF-2 protein product(s) are useful to either protect against atrophy during the fasting and/or facilitate regrowth upon reintroduction of oral nutrients.

Hyaline membrane disease of premature infants results in the absence of surfactant production by type II pneumocytes within the lung, resulting in the collapse of the alveoli. KGF-2 protein product(s) are useful to treat and/or prevent hyaline membrane disease.

Smoke inhalation is a significant cause of morbidity and mortality in the week following a burn injury, due to necrosis of the bronchiolar epithelium and the alveoli. KGF-2 protein products are useful treat and/or prevent inhalation injuries.

Emphysema results from the progressive loss of alveoli. KGF-2 protein product(s) are useful to treat and/or prevent emphysema.

Disorders of the pancreas may be endocrine-related such as Type I or Type II diabetes, or may be exocrine-related such as pancreatitis and pancreatic inefficiencies or cystic fibrosis. Patients with diagnosed Type I diabetes require constant exogenous insulin administration. Patients with diagnosed Type II diabetes progress through varying stages of insulin resistance/insufficiency to ultimately also require exogenous insulin administration. KGF-2 protein product(s) are useful to ameliorate, delay and/or circumvent permanent manifestation of diabetes mellitus or as an adjunct in the setting of islet cell transplantation by inducing pancreatic beta cell function in order to normalize blood glucose levels during varying metabolic demands, yet avoid frequent or profound hypoglycemia. Standard models of diabetes are known (Junod et al. (1967), *Proc. Soc. Exp. Bio. Med.* 126(1):201–205; Rerup (1970), *Pharm. Rev.*, 22:485–518; Rossini et al. (1977), *P.N.A.S.*, 74:2485–2489; and Ar'Rajab and Ahren (1993), *Pancreas*, 8:50–57, the disclosures of which are hereby incorporated by reference). A standard model of pancreatic cell proliferation is known (Yi et al. (1994), *American Journal of Pathology*, 145(1):80–85, the disclosure of which is hereby incorporated by reference).

Corneal cells may be damaged by corneal abrasion and/or corneal ulcerations due to chemicals, bacteria or viruses. KGF-2 protein product(s) are useful treat and/or prevent corneal degeneration. Standard in vivo models of corneal cell regeneration are known (Inatomi et al. (1994), *Investigative Opthalmology and Visual Science*, 35(4):1318, Abstract 299; Sotozono et al. (1994), *Investigative Opthalmology and Visual Science*, 35(4):1941, Abstract 317; Wilson et al. (1994), *Investigative Opthalmology and Visual Science*, 35(4):1319, Abstract 301; Wilson et al. (1993), *The FASEB Journal*, 7(3):A493, Abstract 2857; Inatomi et al. (1994), *Investigative Ophthalmology & Visual Science*, 35(4):1318; Wilson et al. (1994), *Experimental Eye Research*, 59(6):665–678; and Sotozono et al. (1995), *Investigative Ophthalmology & Visual Science*, 36(8):1524–1529, the disclosures of which are hereby incorporated by reference).

KGF-2 protein product(s) are useful to treat and/or prevent gum disease. Standard in vivo models of gum disease are known.

KGF-2 protein product(s) are useful to treat and/or prevent ulcerating and/or inflammatory conditions including conditions related to chemotherapy (as discussed above) and/or infection. Standard in vivo models of urinary bladder damage are known (Ford and Hess (1976), *Arch. Intern. Med.*, 136:616–619 and Droller, et al. (1982), *Urol.*, 20:256–258, the disclosures of which are hereby incorporated by reference).

KGF-2 protein product(s) are useful to treat and/or prevent eardrum damage. Standard in vivo models of tympanic membrane perforations are known (Clymer et al. (1996), *Laryngoscope (USA)*, 106(3):280–285, the disclosure of which is hereby incorporated by reference).

KGF-2 protein product(s) are useful to treat and/or prevent disorders or damage to salivary gland tissue, including radiation/chemotherapy effects (as discussed above) and autoimmune diseases such as Sjogren's Syndrome which can cause salivary glandinsufficiency (sicca syndrome). Standard in vivo models of salivary gland tissue damage are known.

The following examples are included to more fully illustrate the present invention. It is understood that modifications can be made in the procedures set forth without departing from the spirit of the invention.

EXAMPLES

Standard methods for many of the procedures described in the following examples, or suitable alternative procedures, are provided in widely recognized manuals of molecular biology such as, for example, Sambrook et al. (1989), supra and Ausubel et al. (1990), supra. All chemicals are either analytical grade or USP grade.

Example 1

Protein Production

The following example teaches the production of the following KGF-2 protein(s): dN29 hFGF10, dN20 hFGF10, hFGF10 and hFGF10 R149Q.

Please note that the numbering of the "dN" designation is based on the number of amino acids deleted from the normal N-terminal of the rat full-length sequence. Human FGF10 has fewer amino acids at the N-terminal than rat FGF10. The number does not include the methionine added by *E. coli* expression. The amino acid sequence of dN37 rFGF10 is identical to dN29 hFGF10. The amino acid sequence of dN28 rFGF10 is identical to dN20 hFGF10.

A. Preparation of DNA
pAMG21 dN29 rFGF10:

The plasmid pAMG21 dN29 hFGF10 contains DNA encoding the amino acid sequence set forth in FIG. 2 (dN29 hFGF10). The plasmid pAMG21 dN29 hFGF10 contains a truncation of the DNA encoding the 37 amino-terminal residues from the mature rFGF10 sequence, with the truncation having the following N-terminal amino acid sequence: MSYNHLQ . . . (beginning at residue #76, FIG. 2, Yamasaki et al., (1996), supra). Thus, dN29 hFGF10 has the sequence of $Ser^{69}$ to $Ser^{208}$ of SEQ ID NO:2 (ΔN32 KGF-2). pAMG21 dN29 hFGF10 was created as follows.

First, plasmid pAMG21 dN6 rFGF10 was constructed. For this construction, PCR was performed using mature rat FGF10 cDNA (Yamasaki et al. (1996), *J. Biol. Chem.*, 271(27):15918–15921, rFGF) in the vector pGEM-T (Promega, Madison, Wis.), termed pGEM-T rFGF10, as a template with the following 5' oligonucleotide primer (OLIGO#1), which incorporates an NdeI site, and 3' oligonucleotide primer (OLIGO#2) which incorporates a BamHI site:

OLIGO#1: (SEQ ID NO:42) 5'-AAA CAA CAT ATG GTT TCT CCG GAG GCT ACC AAC TCC-3'

OLIGO#2: (SEQ ID NO:43) 5'-AAA CAA GGA TCC TTT ATG AGT GGA CCA CCA TGG GG-3'

The PCR product generated in this reaction was purified and digested with restriction endonucleases NdeI and BamHI. The 525 base pair (bp) restriction-digested PCR product was purified from an agarose gel and ligated with a similarly purified 6 Kilobase (Kb) BamHI to NdeI pAMG21 vector DNA fragment. [The expression vector pAMG21 (ATCC accession no. 98113) contains appropriate restriction sites for insertion of genes downstream from a luxPR promoter (see U.S. Pat. No. 5,169,318 for description of the lux expression system).] The resultant encoded rFGF10 protein differs from rFGF10 by deletion of the first 6 amino-terminal amino acid residues to a naturally occurring methionine residue, with the protein having the following amino-terminal (N-terminal) amino acid sequence: MVSPEAT . . . (beginning at residue #43, FIG. 2, Yamasaki et al. (1996), supra).

Next, the plasmid pAMG21 His rFGF10 was constructed using a pAMG21 His vector. The pAMG21 His vector differs from pAMG21 as follows: between the initiating methionine codon of pAMG21 (ATG) and the sequence that follows it (GTTAACG . . . ), the following sequence is inserted "AAA CAT CAT CAC CAT CAC CAT CAT GCT AGC" which codes for "KHHHHHHHAS". The addition of the codons for Ala and Ser after the 7xHis tag afford a convenient restriction site, NheI, for cloning.

The 4.7 Kb BstXI-NheI fragment of pAMG21 His plasmid vector was then ligated with the 1.8 Kb BspEI-BstXI fragment of pAMG21 dN6 rFGF10 and the following oligonucleotide linkers OLIGO#3 and OLIGO#4 (NheI to BspEI).

OLIGO#3: (SEQ ID NO:44) 5'-CTA GCG ATG ACG ATG ATA AAC AGG CTC TGG GTC AGG ACA TGG TTT CT-3'

OLIGO#4: (SEQ ID NO:45) 5'-CCG GAG AAA CCA TGT CCT GAC CCA GAG CCT GTT TAT CAT CGT CAT CG-3'

The resultant encoded protein differs from dN6 rFGF10 by having a histidine tag (7xHis) followed by an enterokinase cleavage site with the full-length (mature) N-terminal sequence (beginning at residue #37, FIG. 1, Yamasaki et al. (1996), supra). Twenty-two amino acids were added to the amino-terminus of the dN6 rFGF10 as follows: MKHHHHHHHASDDDDKQALGQD[MVSPEAT . . . ].

pAMG21 His rFGF10 was used as a template for PCR amplification using the following 5' oligonucleotide primer (OLIGO#5) which incorporates an NdeI site, and 3' oligonucleotide primer (OLIGO#6) which incorporates a BamHI site:

OLIGO#5: (SEQ ID NO:46) 5'-GGA GGA ATA ACA TAT GTC CTA CAA TCA CCT GCA GGG AGA TGT CCG-3'

OLIGO#6: (SEQ ID NO:47) 5'-AAA CAA GGA TCC TTT ATG AGT GGA CCA CCA TGG GG-3'

The PCR product generated in this reaction was purified and then used as a template for subsequent PCR amplification with the following 5' oligonucleotide primer (OLIGO#7) which incorporates an XbaI site, and 3' oligonucleotide primer (OLIGO#8) which incorporates a BamHI site:

OLIGO#7: (SEQ ID NO:48) 5'-TTA GAT TCT AGA TTT GTT TTA ACT AAT TAA AGG AGG AAT AAC ATA TG-3'

OLIGO#8: (SEQ ID NO:49) 5'-AAA CAA GGA TCC TTT ATG AGT GGA CCA CCA TGG GG-3'

The PCR product generated in this reaction was purified and digested with restriction endonucleases BamHI and XbaI. The 465 bp restriction-digested product was purified from an agarose gel and ligated with a similarly purified 6 Kb pAMG21 BamHI-XbaI DNA fragment to form pAMG21 dN29 hFGF10.

*E. coli* host strain GM120 (ATCC accession no.55764) has the lacIQ promoter and lacI gene integrated into a second site in the host chromosome of a prototrophic *E. coli* K12 host. Transformation of GM120 *E. coli* host with this ligation mixture and plating on Luria agar plates containing 40 μg/ml kanamycin yielded recombinant bacterial colonies.

A bacterial clone containing the correct recombinant plasmid was identified by PCR screening. Plasmid DNA was purified and sequenced to confirm the insert sequence. Growth of recombinant bacterial cultures to express the gene product is described below.

pAMG21 dN20 hFGF10:

The plasmid pAMG21 dN20 hFGF10 contains DNA encoding the amino acid sequence set forth in FIG. 3 (dN20hFGF10). The plasmid pAMG21 dN20 hFGF10 contains a deletion of the DNA encoding the first 28 amino acids of the mature rFGF10 sequence resulting in the following N-terminal amino acid sequence: MSSPSSA . . . (beginning at residue #65. FIG. 2, Yamasaki et al. (1996), supra). plasmid. Thus dN20 hFGF10 has the sequence of $Ser^{58}$ to $Ser^{208}$ of SEQ ID NO:2 (ΔN21 KGF-2).

pAMG21 dN20 hFGF10 was constructed as follows.

The 6 Kb BamHI-NdeI pAMG21 vector fragment was ligated to an NdeI-BamHI dN20 hFGF10 PCR product generated as follows: PCR was carried out using pGEM-T rFGF10 as the template and the following 5' oligonucleotide primer (OLIGO#9) which incorporates an NdeI site at the 5' end of the rFGF10 gene and deletes codons for the first 28 amino acids, and 3' oligonucleotide primer (OLIGO#10) which incorporates a BamHI site at the 3' end of the rFGF10 gene:

OLIGO#9: (SEQ ID NO:50) 5'-AAA CAA CAT ATG TCT TCT CCT TCC TCT GCA GGT AGG CAT GTG CGG AGC TAC AA-3'

OLIGO#10: (SEQ ID NO:51) 5'-AAA CAA GGA TCC TTT ATG AGT GGA CCA CCA TGG GG-3'

This PCR product was purified, digested with restriction endonucleases NdeI and BamHI and, as described above, ligated to the 6 Kb BamHI-NdeI pAMG21 vector fragment.

Transformation of GM120 *E. coli* host with this pAMG21 dN20 hFGF10 ligation product and plating on Luria agar plates containing 40 μg/ml kanamycin yielded recombinant bacterial colonies. A bacterial clone containing the correct recombinant plasmid was identified by PCR screening. Plasmid DNA was purified and sequenced to confirm the insert sequence. Growth of recombinant bacterial cultures to express the gene product is described below. pAMG21 hFGF10 R149Q:

The plasmid pAMG21 hFGF10 R149Q replaces an arginine residue at position 149 in hFGF10 ($Leu^{40}$ to $Ser^{208}$ of SEQ ID NO:2) with a glutamine residue (FIG. 4). pAMG21 hFGF10 R149Q was constructed as follows.

The plasmid pAMG21 rFGF10 was created by ligation of the 6.5 Kb BspEI-NdeI fragment of pAMG21 His rFGF10 with the following oligonucleotide linkers OLIGO#11 and OLIGO#12 (NdeI to BspEI).

OLIGO#11: (SEQ ID NO:52) 5'-TAT GCT GGG TCA GGA CAT GGT TTC T-3'

OLIGO#12: (SEQ ID NO:53) 5'-CCG GAG AAA CCA TGT CCT GAC CCA GCA-3'

The resultant encoded protein differs from His rFGF10 by deletion of the 7×Histidine tag and restoration of the original mature amino terminal protein sequence (MLGQDM . . . ).

A 4.8 Kb BstXI-BspEI fragment of pAMG21 rFGF10 was ligated with the 1.8 Kb fragment of pAMG21 dN20 hFGF10 PstI (introduced)-BstXI and the following OLIGO#13 and OLIGO#14 oligonucleotide linkers (PstI to BspEI) to delete eight serine codons from the rat sequence.

OLIGO#13: (SEQ ID NO:54) 5'-CCG GAG GCT ACC AAC TCT AGC TCC AGC AGC TTC TCC TCT CCT AGC TCT GCA-3'

OLIGO#14: (SEQ ID NO:55) 5'-GAG CTA GGA GAG GAG AAG CTG CTG GAG CTA GAG TTG GTA GCC T-3' pAMG21 hFGF10 R149Q was constructed by the ligation of the 6.1 Kb pAMG21 hFGF10 BamHI-PstI fragment with a hFGF10 R149Q PstI-BamHI PCR product. This PCR product was created as follows:

PCR A was performed using pAMG21 dN29 hFGF10 as the template with the following 5' oligonucleotide primer (OLIGO#15) and 3' oligonucleotide primer (OLIGO#16), which introduces a codon change AGA→CAG:

OLIGO#15: (SEQ ID NO:56) 5'-AAC ACC TAT GCA TCT TTT AAC TGG C-3'

OLIGO#16: (SEQ ID NO:57) 5'-GTC CCT GCC TGG GAG CTC CTT TTC CAT TC-3'

PCR B was performed using pAMG21 dN29 hFGF10 as the template with the following 5' oligonucleotide primer (OLIGO#17), which introduces a codon change, and 3' oligonucleotide primer (OLIGO#18), which incorporates a BamHI site:

OLIGO#17: (SEQ ID NO:58) 5'-GCT CCC AGG CAG GGA CAA AAA ACA AGA AGG-3'

OLIGO#18: (SEQ ID NO:59) 5'-AAC AAA GGA TCC TTT ATG AGT GGA CCA CC-3'

The products of PCR amplifications A and B above were purified and subsequent PCR was performed using them as template with the following 5' oligonucleotide primer OLIGO#19, and OLIGO#20, which incorporates a BamHI site.

OLIGO#19: (SEQ ID NO:60) 5'-AAC ACC TAT GCA TCT TTT AAC TGG C-3'

OLIGO#20: (SEQ ID NO:61) 5'-AAC AAA GGA TCC TTT ATG AGT GGA CCA CC-3'

The product of that reaction was also purified and subsequent PCR was performed using it as template with the following 5' oligonucleotide primer OLIGO#21, which incorporates a BamHI site, and OLIGO#22:

OLIGO#21: (SEQ ID NO:62) 5'-AAC AAA GGA TCC TTT ATG AGT GGA CCA CC-3'

OLIGO#22: (SEQ ID NO:63) 5'-CCG GAG GCT ACC AAC TCT AGC TCC AGC AGC TTC TCC TCT CCT AGC TCT GCA-3'

That final PCR product was purified and digested with restriction endonucleases PstI and BamHI. Following restriction digestion, the 440 bp DNA fragment was gel purified and ligated as described above.

Transformation of GM120 *E. coli* host with this ligation and plating on Luria agar plates containing 40 μg/ml kanamycin yielded recombinant bacterial colonies. A bacterial clone containing the correct recombinant plasmid was identified by PCR screening. Plasmid DNA was purified and sequenced to confirm the insert sequence. Growth of recombinant bacterial cultures to express the gene product is described below.

B. Production in *E. coli*:

Cultures of recombinant GM120 *E. coli* cells containing the DNA sequence-confirmed plasmid of interest (pAMG21 dN29 rFGF10 and pAMG21 hFGF10 R149Q, respectively) are each grown to optimize expression of the introduced gene, as follows:

Five hundred milliliter flasks of Luria Broth plus Kanamycin were seeded with cells and grown at 30° C. degrees from 10 to 16 hours. All 500 mL was added to a 9 L to 11 L of NZ amine-based media in a 15 L fermentor. All batches were grown at a pH of 7 and a dissolved oxygen level of >50%. Batches of cells containing pAMG21 dN29 rFGF10 were grown and induced at 37° C. and of cells containing pAMG21 hFGF10 R149Q were grown and induced at 30° C. The batches were grown at a pH of 7 and a dissolved oxygen level of >50%. When optical cell density reached 10±2, autoinducer was added to the fermentor and cells were allowed to grow for 12 hours. After 12 hours, the broth was chilled to less than 15° C., the fermentor was drained and the cells were collected by centrifugation. The cell paste was frozen.

C. Purification dN29 hFGF10:

dN29 hFGF10 was purified using three chromatography steps: S-Sepharose at pH 7.5, Heparin-Sepharose at pH 7.5, and hydroxyapatite. One hundred grams E. coli cell paste containing dN29 hFGF10 was homogenized and disrupted exactly as described above. Following centrifugation at 15,300×g for 3 hours, the supernatant-containing soluble dN29 hFGF10 was adjusted to 40 mM Tris-HCl, pH 7.5, by addition of 1 M Tris-HCl, pH 7.5, then applied to a 300 mL S-Sepharose FF column equilibrated in 40 mM Tris-HCl, pH 7.5. After washing the column with equilibration buffer to remove unbound protein, the column was eluted with a 40-volume gradient from 0 to 2 M NaCl in 40 mM Tris-HCl, pH 7.5. Fractions eluting between 0.9 M and 1.1 M NaCl contained dN29 hFGF10, which was detected as a 16 kDa band on SDS-PAGE. The identity of this band was confirmed by N-terminal sequencing. These fractions were pooled, diluted with 40 mM Tris-HCl, pH 7.5, to reduce the NaCl concentration to 0.4 M, and applied to a 60 mL Heparin-Sepharose column equilibrated in 40 mM Tris-HCl, pH 7.5. The column was washed with equilibration buffer to remove unbound protein, then eluted with an 80-volume gradient from 0 to 3 M NaCl in the same buffer. dN29 hFGF10 eluted between 1.0 M and 1.35 M NaCl. These fractions were pooled and dialyzed against 40 mM Tris-HCl, pH 7.5. The dialyzed sample was applied to a 50 mL hydroxyapatite column equilibrated in 40 mM Tris-HCl, pH 7.5. Following sample application the column was washed with equilibration buffer to remove unbound protein, then eluted with a 40-volume gradient from 0 to 0.5 M NaCl. Fractions eluting between 0.24 M and 0.44 M NaCl contained dN29 hFGF10. These fractions were pooled, concentrated, and buffer-exchanged to PBS. Sample purity was estimated to be greater than 97% by Coomassie Blue-stained SDS-gels. The yield of purified dN29 hFGF10 was 90 mg from 100 g cell paste.

hFGF10 R149Q:

hFGF10 R149Q was purified exactly as described above for dN29 hFGF10. Human R149Q FGF10 had a lower binding affinity for Heparin-Sepharose than dN29 hFGF10, eluting between 0.5–0.8 M NaCl. The identity and purity of hFGF10 R149Q was analyzed by N-terminal sequencing, and SDS-gel electrophoresis.

Example 2

In Vitro Bioassay

The bioactivity of purified dN29 hFGF10 was assessed by the Balb/MK mouse keratinocyte proliferation assay, which is designed to measure specific activity.

For the Balb/MK keratinocyte assay, 0.5 mg/mL stock solutions of dN29 hFGF10 in PBS was prepared. These samples were serially diluted into assay medium and 50 mL of each dilution was added to tissue culture wells containing Balb/MK cells in 180 mL assay medium. The final concentration of dN29 hFGF10 ranged from $1.2 \times 10^{-1}$ ng/mL to $2.2 \times 10^{4}$ ng/mL. Cell proliferation was measured by uptake of tritiated thymidine.

The estimated $ED_{50}O$ value for dN29 hFGF10 was 46 ng/mL. The results show that dN29 hFGF10 is effective in this assay.

Example 3

Exploratory Studies in Normal Mice

In the first study, 18 female BDF1 mice were divided into 6 groups of 3 mice each (1 treated and 1 control group at each of 3 time points). The first two groups received 5 mg/kg dN29 hFGF10 or the buffer control IV for 1 day, the second two groups received 5 mg/kg dN29 hFGF10 or the buffer control IV daily for 3 days, and the third two groups received 5 mg/kg dN29 hFGF10 or the buffer control IV daily for 7 days. All mice were injected with 50 mg/kg BrdU one hour prior to harvest, radiographed, and sacrificed. Body and selected organ weights (including all segments of small intestine) were taken, blood was drawn for hematology and serum chemistries, and organs were harvested for histologic analysis and BrdU labeling. There was some elevation of stomach on day 7, liver on day 3, jejenum on day 7. There was no effect on thymus. The serum chemistries were variable and normalize very rapidly.

Example 4

Chemotherary-induced Pulmonary Fibrosis

Male Lewis rats weighing approximately 225 grams received an i.v. injection or intratracheal instillation of 5 mg/kg of dN29 hFGF10 or vehicle 72 and 48 hours prior to receiving 2.5U of bleomycin via the intratracheal route. Rat weight was monitored over the course of the following 15 days at which time pulmonary function tests were performed in the rats that had received the dN29 hFGF10 via the intratracheal route. For histology, catheters was placed in the trachea of each rat and the lungs were filled with 3 ml of formalin via hydrostatic pressure. Following fixation for 48 hours and the lungs were processed into paraffin for sectioning and staining.

Rats receiving saline administration lost 42% of their body weight while those treated with dN29 hFGF10 were are 129% of their weight compared to the day of bleomycin administration. One rat in the saline group died before the time of sacrifice, this death is assumed to be from the insult of bleomycin to the lung. There was a significant difference in pulmonary respiratory rate and tidal volume between the two groups. Rats treated with saline had a respiration rate of 286 breaths per minute compared with 247 for the dN29 hFGF10 group. Untreated control rats had respiratory rate of 216 breaths per minute which is significant vs. the dN29 hFGF10 group at the $p<0.05$ level.

Histologically, there was gross and microscopic changes to the saline treated group. The lungs in this group were deformed, as was observed at the time of sacrifice, and had excessive inflammation and fibrosis. Lungs of the dN29 hFGF10 group were very similar to those of the untreated controls with the exception of having focal mild microscopic inflammation. There was no distinguishable gross difference between the dN29 hFGF10 and normal rats.

Example 5

Radiation-induced Mucositis Model

Mucositis is induced in mice with 12 Gy of whole-body radiation. Mice are treated daily with 5 mg/kg/day of recombinant human KGF-2 (prepared generally in accordance with the teachings of WO 96/25422, rhuKGF-2) beginning on the day before radiation and continuing to day three post-radiation. Four days after radiation, the mice are necropsied and the number of proliferating crypts (containing BUdR-positive cells) are counted.

rhuKGF-2 treatment increases the number of proliferating crypts in the duodenum, proximal and distal jejunum of the small intestine relative to non-rhuKGF-2 treated animals. rhuKGF-2 is also able to decrease the body weight loss in the irradiated mice.

Example 6

Adriamycin-induced Mucositis Model

Mucositis is induced in mice with a single intraperitoneal dose of Adriamycin at 24 mg/kg. Mice are treated daily with 1 mg/kg/day of rhuKGF-2 beginning on the day before radiation and continuing to day three post-radiation. Four days after radiation, the mice are necropsied and the number of proliferating crypts (containing BUdR-positive cells) are counted.

rhuKGF-2 treatment increases the number of proliferating crypts in the duodenum, jejunum and ileum relative to non-rhuKGF-2 treated animals.

Example 7

5-Fluorouracil-induced Mucositis Model

Mice are injected with 5-fluorouracil (5-FU, 50 mg/kg/day×4 days), a regimen that in non-treated animals leads to a survival ranging only between 20–50%. rhuKGF-2 pre-treatments (5 mg/kg/day×3 days), but not post-treatments, increase survival relative to non-rhuKGF-2 treated animals and improvements in survival are seen at doses as low as 0.5 mg/kg/day. Hepatic abscesses are commonly found in control, but not rhuKGF-2-pretreated, surviving mice indicating that 5-FU's toxicity is in part due to loss of the GI barrier function. In addition, rhuKGF-2-pretreated mice lose less weight and consume more food and water during the 5-FU treatment period. rhuKGF-2 pretreatments also ameliorate weight loss in mice following carboplatin (125 mg/kg×1 day) exposure, excluding the possibility that rhuKGF's effects are 5-FU specific. rhuKGF-2 pretreatments also improve survival and weight loss nadirs in chemotherapy/radiation combination experiments when mice are injected with a single dose of 150 or 300 mg/kg of methotrexate followed by irradiation (6 Gy) 1 hour later.

Example 8

Colitis Model

In two groups of 10 animals each, colitis is induced by colonic instillation of 2,4,6-trinitrobenzenesulfonic acid in ethanol at a dose of 50 mg/kg body weight. To determine if rhuKGF-2 acts through a protective mechanism, one group of rats (group A) is pretreated with rhuKGF-2 or vehicle at 24 hours and at 1 hour prior to induction of colitis at a dose of 5 mg/kg (i.p.) and the animals are sacrificed 8 hours after injury. To assess potential healing effects, rhuKGF-2 or vehicle (same dosage, i.p.) is injected in a second group (group B) 24 hours after induction of colitis and treatment is continued daily for 1 week. Tissue damage is examined microscopically and is expressed as percentage of ulcerations or erosions.

Animals which are treated with rhuKGF-2 after induction of colitis (group B) show significantly less ulcerations compared to the control group (group A). In animals treated prior to induction of colitis, there are erosions, but no ulcers are seen due to the short study period of 8 hours, and the erosions are not significantly different from those seen in the control group (group A).

Example 9

Dextran Sulfate-induced Colitis Model

Study 1: Rats are fed 4% and 6% DSS in water for 1 week. At the end of the second week the distal 4 cm of the colon is preserved. Eight sections at 0.5 cm intervals are prepared and stained with H & E. The percent of each colon section with necrosis (destruction of the glandular structure) is assessed in a randomized and coded fashion.

Study 2: Rats are given IP vehicle or rhuKGF-2 (1 mg/kg/day) and fed either water or 4% dextran sulfate sodium for 14 days. The colonic sections are stained with PAS.

Dextran sulfate sodium appears to induce a dose-related increase in colonic mucosal necrosis. rhuKGF-2 administered at 1 mg/kg/day for 14 days increases colonic mucin production in the control group as well as in the dextran sulfate sodium-treated rats.

Example 10

Rat Cirrhosis Model

Male Sprague-Dawley rats weighing between 150 and 175 gms are used. Animals are exposed to phenobarbitol (0.35 mg/ml) in their drinking water for the duration of the study. Animals are dosed weekly with CC14 in a corn oil vehicle while under light isoflurance anesthesia. The initial dose of CC14 is 40 $\mu$l per rat. The dose is adjusted weekly, up or down in 40 $\mu$l increments based on weight gain. Ten control animals are exposed to phenobarbitol in their drinking water and lavaged weekly with corn oil vehicle. Liver function is assessed by measurement of bromosulphopthylein (BSP) clearance, serum transaminase levels and serum albumin levels. At the time of sacrifice, livers are removed, weighed and processed for determination of hydroxyproline levels as an indicator of collagen deposition and fibrosis.

Animals are maintained on the above cirrhosis induction protocol for 11 weeks. In the eleventh week, animals are randomized into control and rhuKGF-2 treatment groups. rhuKGF-2 is given once per day by subcutaneous injection at a dose of 1 mg/kg, for a total of 15 days. After 15 days of rhuKGF-2 treatment, the animals are euthanized.

Rats in which cirrhosis is induced with CC14 show an elevation in serum BSP concentration, reflecting impaired liver clearance of this agent. Rats treated with rhuKGF-2 have a lower BSP serum level than untreated animals, suggesting an improved liver function. Rats made cirrhotic by CC14 show an elevation in SGPT which is reversed by rhuKGF-2 treatment. rhuKGF-2 treatment is able to elevate serum albumin. rhuKGF-2 treatment results in an increased liver-to-body weight ratio, reflecting compensatory liver growth.

Example 11

Hepatectomy Model

Rats subjected to a 70% partial hepatectomy recover their original liver mass more quickly when treated with 1 mg/kg/d rhuKGF-2 than when compared to untreated animals.

Example 12

Acute Hepatotoxicity Models

In acute hepatotoxicity models, rhuKGF-2 treatment (1 mg/kg either prior to or 3 hr after the inciting agent) blunts increases in serum transaminase levels in rats with acute hepatic failure induced with either carbon tetrachloride, acetaminophen or galactosamine. Pretreatment with rhuKGF-2 also prevents a decrease in liver clearance functions after acetaminophen, as measured by sulfobromophthalein (BSP) clearance.

Example 13

In Vivo Retro-viral-mediated Gene Transfer Model

Mice are intraveneously administered with rhuKGF-2 (1–5 mg/kg). 48 hours after intravenous injection of rhuKGF-2, murine hepatocyte proliferation increases, compared to non-stimulated livers, and returns to normal proliferative levels. No modules or microscopic abnormalities are noted either acutely or after 5 months.

When rhuKGF-2 treatment is followed by intravenous injection of high titer *E. coli* LacZ expressing Moloney retroviral vectors (1×108 cfu.ml), β-galactosidase expression increases with a percentage of the hepatocytes being transduced. Several months later, a portion of the transduced hepatocytes remain X-gal positive.

Example 14

In Vivo Model of Diabetes

Male rats weighing 200 to 260 grams at study initiation are used in this model (WO 9611950). Diabetes is induced by a single intravenous injection of streptozotocin at 50 mg of streptozotocin in sodium citrate buffer per kg of body weight. Non-diabetic control rats receive a single intravenous injection of sodium citrate buffer for control purposes. rhuKGF-2 is administered daily as a subcutaneous injection. The rhuKGF-2 dose is 3 or 5 mg/kg/day, depending upon the experiment.

In the first experiment, rhuKGF-2 therapy is initiated two days before diabetes, is induced and continued after the induction of diabetes for a total of eight injections. Those diabetic rats which are treated with rhuKGF-2 prior to diabetes induction, and for which rhuKGF-2 is also continued after the induction, show symptoms indicative of a milder form of diabetes. Thus, rhuKGF-2 therapy either partially prevents induction of the disease or restores insulin-producing islet cells after streptozotocin-induced beta cell destruction.

In the second and third experiments, rhuKGF-2 therapy administered subcutaneously is initiated one day after the induction of diabetes with streptozotocin. In the second study, fasting water intake and urine output are significantly less in the rhuKGF-2-treated diabetic rats when compared to diabetic rats on day 9, which is further indicative of amelioration of the disease condition. In the third study, rhuKGF-2 therapy is able to increase the total content of insulin and C-peptide in the pancreas of diabetic rats when compared to diabetic rats treated with sodium chloride solution.

In the fourth experiment, a 7-day course of rhuKGF-2 therapy is initiated 7 days after streptozotocin treatment and the animals are then followed for an additional 12 weeks. In all experiments, except for the fourth experiment, blood glucose levels, urine glucose levels and urine volume are used as end points for analysis. Additionally, water intake, urine C-peptide levels, or total pancreatic insulin and C-peptide content are measured in some experiments. In the fourth experiment, the only assessed endpoint is blood glucose.

Because a large fraction of insulin is removed from the circulation by the liver, measurement of peripheral insulin concentrations reflects post-hepatic metabolism events rather than insulin secretion from the pancreas. Therefore, measurements of C-peptide are often made and used as a peripheral marker of insulin secretion. C-peptide is produced from the processing of pro-insulin to insulin. Insulin and C-peptide are secreted from the beta cells in equimolar amounts, and only a small amount of C-peptide is extracted by the liver.

STZ-treated animals from both groups receiving rhuKGF-2 have significant declines in blood glucose during the rhuKGF-2 dosing period.

Example 15

Hyperoxia-induced Mortality Model

To determine the effect of rhuKGF-2 administration on hyperoxia-induced lung injury, rats are treated by intratracheal instillation and exposed to >98% oxygen for up to 120 hours. At necropsy, after 120 hours of hyperoxia exposure, the lungs of rhuKGF-2 treated animals appear grossly normal, with few scattered areas of puncture hemorrhage on the pleural surface, compared with the grossly hemorrhagic lungs of untreated rats dying between 55 and 80 hours of hyperoxia exposure.

Histopathologically, the lungs of untreated animals demonstrate large areas of hemorrhage and interstitial edema. The intraaveolar space contains red blood cells, inflammatory cells, and proteinaceous exudate. In contrast, there is no intraaveolar exudate and minimal evidence of hemorrhage in the lungs of the animals treated with rhuKGF-2 who survive for 120 hours in hyperoxia.

At doses of 5 and 1 mg/kg, rhuKGF-2 significantly decreases hyperoxia-induced mortality.

Example 16

Acute Lung Injury Model

Acute permeability pulmonary edema is induced with an injection of α-naphthylthiourea, and lung leak is assessed in an isolated perfused lung model over 180 minutes. Leakage is confirmed with wet/dry lung weight ratios, and the alveolar fluid protein concentration is measured after bronchoalveolar lavage. The effect of pretreatment with rhuKGF-2 (injected intratracheally 48 hours before the experiment) on α-naphthylthiourea-induced pulmonary edema is assessed (rhuKGF-2/α-naphthylthiourea group). Control groups (Control and rhuKGF-2/Control) are also studied. Histopathology is performed for each of the four groups.

The α-naphthylthiourea produces an acute permeability pulmonary edema detected by lung leak over the 180-minute ex vivo period of monitoring the isolated perfused lung. Pretreatment with rhuKGF-2 significantly attenuates these parameters which are not significantly different from the control group and the rhuKGF-2/control group. Histopathology shows abundant type II pneumocyte hyperplasia in the lungs of animals pretreated with rhuKGF-2, and marked pulmonary edema in animals pretreated with α-naphthylthiourea. Less edema is apparent in the rhuKGF-2/α-naphthylthiourea group.

While the present invention has been described above both generally and in terms of preferred embodiments, it is understood that other variations and modifications will occur to those skilled in the art in light of the description above.

We claim:

1. A keratinocyte growth factor-2 (KGF-2) protein selected from the group consisting of:

(a) a KGF-2 protein consisting of residues 66 through 208 of the amino acid sequence set forth in SEQ ID NO: 2; and (b) a KGF-2 protein consisting of residues 66 through 208 of the amino acid sequence set forth in SEQ ID NO: 2 and an N-terminal methionine.

2. The KGF-2 protein according to claim 1, wherein said amino acid sequence is nonglycosylated.

3. The KGF-2 protein according to claim 1, wherein said amino acid sequence is glycosylated.

4. A chemical derivative comprising a water-soluble polymer conjugated to the KGF-2 protein according to claim 1.

5. A polynucleotide encoding the KGF-2 protein according to claim 1.

6. A vector comprising a polynucleotide of claim 5 operatively linked to an expression control sequence.

7. A prokaryotic or eukaryotic host cell containing a polynucleotide of claim 5.

8. A method comprising culturing the host cell of claim 7 in a suitable nutrient medium.

9. The method according to claim 8, wherein said host cell is an *E. coli* cell.

10. The method according to claim 8, wherein said host cell is selected from a baculovirus cell, COS cell or Chinese hamster ovary cell.

11. The method of claims 8, 9 or 10 further comprising isolating a keratinocyte growth factor-2 (KG F-2) protein from said cultured cells or said nutrient medium.

12. A pharmaceutical composition comprising a keratinocyte growth factor-2 (KGF-2) protein isolated in accordance with the method of claim 11 in association with a pharmaceutically acceptable vehicle.

13. A method comprising the step of isolating a keratinocyte growth factor-2 (KGF-2) protein from a host cell containing a polynucleotide of claim 5 cultured under conditions allowing the expression of the KGF-2 protein by said host cell.

14. The method according to claim 13 comprising the step of conjugating the isolated KGF-2 protein to a water-soluble polymer to generate a compound capable of stimulating the production of epithelial cells.

15. A method comprising the steps of:
    (a) culturing a prokaryotic or eukaryotic host cell containing a polynucleotide of claim 5; and
    (b) maintaining said host cell under conditions allowing the expression of a keratinocyte growth factor-2 (KGF-2) protein by said host cell.

16. The method of claim 15, further comprising after step (b) the following step (c):
    (c) isolating the KGF-2 protein expressed by said host cell.

17. A pharmaceutical composition comprising a keratinocyte growth factor-2 (KGF-2) protein isolated in accordance with the method of claim 16 in association with a pharmaceutically acceptable vehicle.

18. A KGF-2 protein which is the recombinant expression product of a prokaryotic or eukaryotic host cell containing an exogenous polynucleotide of claim 5.

19. A pharmaceutical composition comprising the KGF-2 protein according to claim 1 in association with a pharmaceutically acceptable vehicle.

20. The KGF-2 protein according to claim 1, wherein at least one domain of the constant region of the heavy chain of human immunoglobulin is fused to the C-terminal end of the KGF-2 protein.

21. A recombinant fusion protein comprising the KGF-2 protein of claim 1 fused to a heterologous protein.

* * * * *

SEQUENCE LISTING

<160> NUMBER OF SEQ ID NOS: 63

<210> SEQ ID NO 1
<211> LENGTH: 627
<212> TYPE: DNA
<213> ORGANISM: Recombinant Human
<220> FEATURE:
<221> NAME/KEY: CDS
<222> LOCATION: (1)..(624)

<400> SEQUENCE: 1

```
atg tgg aaa tgg ata ctg aca cat tgt gcc tca gcc ttt ccc cac ctg      48
Met Trp Lys Trp Ile Leu Thr His Cys Ala Ser Ala Phe Pro His Leu
 1               5                  10                  15 ccc ggc tgc tgc tgc tgc ttt ttg ttg ctg ttc ttg gtg tct tcc          96
Pro Gly Cys Cys Cys Cys Phe Leu Leu Leu Phe Leu Val Ser Ser
             20                  25                  30 gtc cct gtc acc tgc caa gcc ctt ggt cag gac atg gtg tca cca gag     144
Val Pro Val Thr Cys Gln Ala Leu Gly Gln Asp Met Val Ser Pro Glu
         35                  40                  45 gcc acc aac tct tct tcc tcc tcc ttc tcc tct cct tcc agc gcg gga     192
Ala Thr Asn Ser Ser Ser Ser Ser Phe Ser Ser Pro Ser Ser Ala Gly
     50                  55                  60 agg cat gtg cgg agc tac aat cac ctt caa gga gat gtc cgc tgg aga     240
Arg His Val Arg Ser Tyr Asn His Leu Gln Gly Asp Val Arg Trp Arg
 65                  70                  75                  80 aag cta ttc tct ttc acc aag tac ttt ctc aag att gag aag aac ggg     288
Lys Leu Phe Ser Phe Thr Lys Tyr Phe Leu Lys Ile Glu Lys Asn Gly
                 85                  90                  95 aag gtc agc ggg acc aag aag gag aac tgc ccg tac agc atc ctg gag     336
Lys Val Ser Gly Thr Lys Lys Glu Asn Cys Pro Tyr Ser Ile Leu Glu
            100                 105                 110 ata aca tca gta gaa atc gga gtt gtt gcc gtc aaa gcc att aac agc     384
Ile Thr Ser Val Glu Ile Gly Val Val Ala Val Lys Ala Ile Asn Ser
        115                 120                 125 aac tat tac tta gcc atg aac aag aag ggg aaa ctc tat ggc tca aaa     432
Asn Tyr Tyr Leu Ala Met Asn Lys Lys Gly Lys Leu Tyr Gly Ser Lys
    130                 135                 140 gaa ttt aac aat gac tgt aag ctg aag gag agg ata gag gaa aat gga     480
Glu Phe Asn Asn Asp Cys Lys Leu Lys Glu Arg Ile Glu Glu Asn Gly
145                 150                 155                 160 tac aat acc tat gca tca ttt aac tgg cag cat aat ggg agg caa atg     528
Tyr Asn Thr Tyr Ala Ser Phe Asn Trp Gln His Asn Gly Arg Gln Met
                165                 170                 175 tat gtg gca ttg aat gga aaa gga gct cca agg aga gga cag aaa aca     576
Tyr Val Ala Leu Asn Gly Lys Gly Ala Pro Arg Arg Gly Gln Lys Thr
            180                 185                 190 cga agg aaa aac acc tct gct cac ttt ctt cca atg gtg gta cac tca     624
Arg Arg Lys Asn Thr Ser Ala His Phe Leu Pro Met Val Val His Ser
        195                 200                 205 tag                                                                  627
```

<210> SEQ ID NO 2
<211> LENGTH: 208
<212> TYPE: PRT
<213> ORGANISM: Recombinant Human

<400> SEQUENCE: 2

```
Met Trp Lys Trp Ile Leu Thr His Cys Ala Ser Ala Phe Pro His Leu
 1               5                  10                  15
```

```
Pro Gly Cys Cys Cys Cys Phe Leu Leu Leu Phe Leu Val Ser Ser
            20                  25                  30

Val Pro Val Thr Cys Gln Ala Leu Gly Gln Asp Met Val Ser Pro Glu
        35                  40                  45

Ala Thr Asn Ser Ser Ser Ser Phe Ser Ser Pro Ser Ser Ala Gly
    50                  55                  60

Arg His Val Arg Ser Tyr Asn His Leu Gln Gly Asp Val Arg Trp Arg
65              70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val His Ser
        195                 200                 205

<210> SEQ ID NO 3
<211> LENGTH: 426
<212> TYPE: DNA
<213> ORGANISM: Recombinant Human
<220> FEATURE:
<221> NAME/KEY: CDS
<222> LOCATION: (1)..(423)

<400> SEQUENCE: 3 atg tcc tac aat cac ctg cag gga gat gtc cgc tgg aga aag ctg ttc      48
Met Ser Tyr Asn His Leu Gln Gly Asp Val Arg Trp Arg Lys Leu Phe
  1               5                  10                  15 tcc ttc acc aag tac ttt ctc aag att gaa aag aac ggc aag gtc agc      96
Ser Phe Thr Lys Tyr Phe Leu Lys Ile Glu Lys Asn Gly Lys Val Ser
                 20                  25                  30 ggg acc aag aag gaa aac tgt ccg tac agt atc cta gag ata aca tca     144
Gly Thr Lys Lys Glu Asn Cys Pro Tyr Ser Ile Leu Glu Ile Thr Ser
             35                  40                  45 gtg gaa atc gga gtt gtt gcc gtc aaa gcc att aac agc aac tat tac     192
Val Glu Ile Gly Val Val Ala Val Lys Ala Ile Asn Ser Asn Tyr Tyr
         50                  55                  60 tta gcc atg aac aag aag ggg aaa ctc tat ggc tca aaa gaa ttt aac     240
Leu Ala Met Asn Lys Lys Gly Lys Leu Tyr Gly Ser Lys Glu Phe Asn
 65                  70                  75                  80 aat gac tgt aaa ctg aaa gag agg ata gag gaa aat gga tac aac acc     288
Asn Asp Cys Lys Leu Lys Glu Arg Ile Glu Glu Asn Gly Tyr Asn Thr
                 85                  90                  95 tat gca tct ttt aac tgg cag cac aac ggc agg caa atg tat gtg gca     336
Tyr Ala Ser Phe Asn Trp Gln His Asn Gly Arg Gln Met Tyr Val Ala
            100                 105                 110 ttg aat gga aaa gga gct ccc agg aga gga caa aaa aca aga agg aaa     384
Leu Asn Gly Lys Gly Ala Pro Arg Arg Gly Gln Lys Thr Arg Arg Lys
        115                 120                 125
```

```
aac acc tcc gct cac ttc ctc ccc atg gtg gtc cac tca taa              426
Asn Thr Ser Ala His Phe Leu Pro Met Val Val His Ser
    130                 135                 140
```

<210> SEQ ID NO 4
<211> LENGTH: 141
<212> TYPE: PRT
<213> ORGANISM: Recombinant Human

<400> SEQUENCE: 4

```
Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
                20                  25                  30

Gly Thr Lys Lys Glu Asn Cys Pro Tyr Ser Ile Leu Glu Ile Thr Ser
            35                  40                  45

Val Glu Ile Gly Val Val Ala Val Lys Ala Ile Asn Ser Asn Tyr Tyr
 50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Arg Lys
        115                 120                 125

Asn Thr Ser Ala His Phe Leu Pro Met Val Val His Ser
    130                 135                 140
```

<210> SEQ ID NO 5
<211> LENGTH: 459
<212> TYPE: DNA
<213> ORGANISM: Recombinant Human
<220> FEATURE:
<221> NAME/KEY: CDS
<222> LOCATION: (1)..(456)

<400> SEQUENCE: 5

```
atg tct tct cct tcc tct gca ggt agg cat gtg cgg agc tac aat cac    48
Met Ser Ser Pro Ser Ser Ala Gly Arg His Val Arg Ser Tyr Asn His
 1               5                  10                  15 ctc cag gga gat gtc cgc tgg aga aag ctg ttc tcc ttc acc aag tac    96
Leu Gln Gly Asp Val Arg Trp Arg Lys Leu Phe Ser Phe Thr Lys Tyr
                20                  25                  30 ttt ctc aag att gaa aag aac ggc aag gtc agc ggg acc aag aag gaa   144
Phe Leu Lys Ile Glu Lys Asn Gly Lys Val Ser Gly Thr Lys Lys Glu
            35                  40                  45 aac tgt ccg tac agt atc cta gag ata aca tca gtg gaa atc gga gtt   192
Asn Cys Pro Tyr Ser Ile Leu Glu Ile Thr Ser Val Glu Ile Gly Val
 50                  55                  60 gtt gcc gtc aaa gcc att aac agc aac tat tac tta gcc atg aac aag   240
Val Ala Val Lys Ala Ile Asn Ser Asn Tyr Tyr Leu Ala Met Asn Lys
 65                  70                  75                  80 aag ggg aaa ctc tat ggc tca aaa gaa ttt aac aat gac tgt aaa ctg   288
Lys Gly Lys Leu Tyr Gly Ser Lys Glu Phe Asn Asn Asp Cys Lys Leu
                85                  90                  95 aaa gag agg ata gag gaa aat gga tac aac acc tat gca tct ttt aac   336
Lys Glu Arg Ile Glu Glu Asn Gly Tyr Asn Thr Tyr Ala Ser Phe Asn
            100                 105                 110
```

```
tgg cag cac aac ggc agg caa atg tat gtg gca ttg aat gga aaa gga       384
Trp Gln His Asn Gly Arg Gln Met Tyr Val Ala Leu Asn Gly Lys Gly
        115                 120                 125 gct ccc agg aga gga caa aaa aca aga agg aaa aac acc tcc gct cac       432
Ala Pro Arg Arg Gly Gln Lys Thr Arg Arg Lys Asn Thr Ser Ala His
130                 135                 140 ttc ctc ccc atg gtg gtc cac tca taa                                   459
Phe Leu Pro Met Val Val His Ser
145                 150

<210> SEQ ID NO 6
<211> LENGTH: 152
<212> TYPE: PRT
<213> ORGANISM: Recombinant Human

<400> SEQUENCE: 6

Met Ser Ser Pro Ser Ser Ala Gly Arg His Val Arg Ser Tyr Asn His
1               5                   10                  15

Leu Gln Gly Asp Val Arg Trp Arg Lys Leu Phe Ser Phe Thr Lys Tyr
                20                  25                  30

Phe Leu Lys Ile Glu Lys Asn Gly Lys Val Ser Gly Thr Lys Lys Glu
            35                  40                  45

Asn Cys Pro Tyr Ser Ile Leu Glu Ile Thr Ser Val Glu Ile Gly Val
        50                  55                  60

Val Ala Val Lys Ala Ile Asn Ser Asn Tyr Tyr Leu Ala Met Asn Lys
65                  70                  75                  80

Lys Gly Lys Leu Tyr Gly Ser Lys Glu Phe Asn Asn Asp Cys Lys Leu
                85                  90                  95

Lys Glu Arg Ile Glu Glu Asn Gly Tyr Asn Thr Tyr Ala Ser Phe Asn
            100                 105                 110

Trp Gln His Asn Gly Arg Gln Met Tyr Val Ala Leu Asn Gly Lys Gly
        115                 120                 125

Ala Pro Arg Arg Gly Gln Lys Thr Arg Arg Lys Asn Thr Ser Ala His
130                 135                 140

Phe Leu Pro Met Val Val His Ser
145                 150

<210> SEQ ID NO 7
<211> LENGTH: 513
<212> TYPE: DNA
<213> ORGANISM: Recombinant Human
<220> FEATURE:
<221> NAME/KEY: CDS
<222> LOCATION: (1)..(510)

<400> SEQUENCE: 7 atg ctg ggt cag gac atg gtt tct ccg gag gct acc aac tct agc tcc        48
Met Leu Gly Gln Asp Met Val Ser Pro Glu Ala Thr Asn Ser Ser Ser
1               5                   10                  15 agc agc ttc tcc tct cct agc tct gca ggt agg cat gtg cgg agc tac        96
Ser Ser Phe Ser Ser Pro Ser Ser Ala Gly Arg His Val Arg Ser Tyr
                20                  25                  30 aat cac ctc cag gga gat gtc cgc tgg aga aag ctg ttc tcc ttc acc       144
Asn His Leu Gln Gly Asp Val Arg Trp Arg Lys Leu Phe Ser Phe Thr
            35                  40                  45 aag tac ttt ctc aag att gaa aag aac ggc aag gtc agc ggg acc aag       192
Lys Tyr Phe Leu Lys Ile Glu Lys Asn Gly Lys Val Ser Gly Thr Lys
        50                  55                  60 aag gaa aac tgt ccg tac agt atc cta gag ata aca tca gtg gaa atc       240
Lys Glu Asn Cys Pro Tyr Ser Ile Leu Glu Ile Thr Ser Val Glu Ile
```

|   |   |   |   |   |   |   |   |   |   |   |   |   |   |   |   |   |
|---|---|---|---|---|---|---|---|---|---|---|---|---|---|---|---|---|
| | | 65 | | | | 70 | | | | 75 | | | | 80 | | |

```
gga gtt gtt gcc gtc aaa gcc att aac agc aac tat tac tta gcc atg      288
Gly Val Val Ala Val Lys Ala Ile Asn Ser Asn Tyr Tyr Leu Ala Met
                85                  90                  95 aac aag aag ggg aaa ctc tat ggc tca aaa gaa ttt aac aat gac tgt      336
Asn Lys Lys Gly Lys Leu Tyr Gly Ser Lys Glu Phe Asn Asn Asp Cys
            100                 105                 110 aaa ctg aaa gag agg ata gag gaa aat gga tac aac acc tat gca tct      384
Lys Leu Lys Glu Arg Ile Glu Glu Asn Gly Tyr Asn Thr Tyr Ala Ser
        115                 120                 125 ttt aac tgg cag cac aac ggc agg caa atg tat gtg gca ttg aat gga      432
Phe Asn Trp Gln His Asn Gly Arg Gln Met Tyr Val Ala Leu Asn Gly
    130                 135                 140 aaa gga gct ccc agg cag gga caa aaa aca aga agg aaa aac acc tcc      480
Lys Gly Ala Pro Arg Gln Gly Gln Lys Thr Arg Arg Lys Asn Thr Ser
145                 150                 155                 160 gct cac ttc ctc ccc atg gtg gtc cac tca taa                          513
Ala His Phe Leu Pro Met Val Val His Ser
                165                 170
```

<210> SEQ ID NO 8
<211> LENGTH: 170
<212> TYPE: PRT
<213> ORGANISM: Recombinant Human

<400> SEQUENCE: 8

```
Met Leu Gly Gln Asp Met Val Ser Pro Glu Ala Thr Asn Ser Ser Ser
 1               5                  10                  15

Ser Ser Phe Ser Ser Pro Ser Ser Ala Gly Arg His Val Arg Ser Tyr
            20                  25                  30

Asn His Leu Gln Gly Asp Val Arg Trp Arg Lys Leu Phe Ser Phe Thr
        35                  40                  45

Lys Tyr Phe Leu Lys Ile Glu Lys Asn Gly Lys Val Ser Gly Thr Lys
    50                  55                  60

Lys Glu Asn Cys Pro Tyr Ser Ile Leu Glu Ile Thr Ser Val Glu Ile
65                  70                  75                  80

Gly Val Val Ala Val Lys Ala Ile Asn Ser Asn Tyr Tyr Leu Ala Met
                85                  90                  95

Asn Lys Lys Gly Lys Leu Tyr Gly Ser Lys Glu Phe Asn Asn Asp Cys
            100                 105                 110

Lys Leu Lys Glu Arg Ile Glu Glu Asn Gly Tyr Asn Thr Tyr Ala Ser
        115                 120                 125

Phe Asn Trp Gln His Asn Gly Arg Gln Met Tyr Val Ala Leu Asn Gly
    130                 135                 140

Lys Gly Ala Pro Arg Gln Gly Gln Lys Thr Arg Arg Lys Asn Thr Ser
145                 150                 155                 160

Ala His Phe Leu Pro Met Val Val His Ser
                165                 170
```

<210> SEQ ID NO 9
<211> LENGTH: 4
<212> TYPE: PRT
<213> ORGANISM: Recombinant Human

<400> SEQUENCE: 9

```
Val Arg Ser Tyr
 1
```

<210> SEQ ID NO 10
<211> LENGTH: 5
<212> TYPE: PRT
<213> ORGANISM: Recombinant Human

<400> SEQUENCE: 10

His Val Arg Ser Tyr
 1               5

<210> SEQ ID NO 11
<211> LENGTH: 6
<212> TYPE: PRT
<213> ORGANISM: Recombinant Human

<400> SEQUENCE: 11

Arg His Val Arg Ser Tyr
 1               5

<210> SEQ ID NO 12
<211> LENGTH: 7
<212> TYPE: PRT
<213> ORGANISM: Recombinant Human

<400> SEQUENCE: 12

Gly Arg His Val Arg Ser Tyr
 1               5

<210> SEQ ID NO 13
<211> LENGTH: 8
<212> TYPE: PRT
<213> ORGANISM: Recombinant Human

<400> SEQUENCE: 13

Ala Gly Arg His Val Arg Ser Tyr
 1               5

<210> SEQ ID NO 14
<211> LENGTH: 9
<212> TYPE: PRT
<213> ORGANISM: Recombinant Human

<400> SEQUENCE: 14

Ser Ala Gly Arg His Val Arg Ser Tyr
 1               5

<210> SEQ ID NO 15
<211> LENGTH: 10
<212> TYPE: PRT
<213> ORGANISM: Recombinant Human

<400> SEQUENCE: 15

Ser Ser Ala Gly Arg His Val Arg Ser Tyr
 1               5                   10

<210> SEQ ID NO 16
<211> LENGTH: 11
<212> TYPE: PRT
<213> ORGANISM: Recombinant Human

<400> SEQUENCE: 16

Pro Ser Ser Ala Gly Arg His Val Arg Ser Tyr
 1               5                   10

<210> SEQ ID NO 17
<211> LENGTH: 12

```
<212> TYPE: PRT
<213> ORGANISM: Recombinant Human

<400> SEQUENCE: 17

Ser Pro Ser Ser Ala Gly Arg His Val Arg Ser Tyr
 1               5                  10

<210> SEQ ID NO 18
<211> LENGTH: 13
<212> TYPE: PRT
<213> ORGANISM: Recombinant Human

<400> SEQUENCE: 18

Ser Ser Pro Ser Ser Ala Gly Arg His Val Arg Ser Tyr
 1               5                  10

<210> SEQ ID NO 19
<211> LENGTH: 14
<212> TYPE: PRT
<213> ORGANISM: Recombinant Human

<400> SEQUENCE: 19

Phe Ser Ser Pro Ser Ser Ala Gly Arg His Val Arg Ser Tyr
 1               5                  10

<210> SEQ ID NO 20
<211> LENGTH: 15
<212> TYPE: PRT
<213> ORGANISM: Recombinant Human

<400> SEQUENCE: 20

Ser Phe Ser Ser Pro Ser Ser Ala Gly Arg His Val Arg Ser Tyr
 1               5                  10                  15

<210> SEQ ID NO 21
<211> LENGTH: 16
<212> TYPE: PRT
<213> ORGANISM: Recombinant Human

<400> SEQUENCE: 21

Ser Ser Phe Ser Ser Pro Ser Ser Ala Gly Arg His Val Arg Ser Tyr
 1               5                  10                  15

<210> SEQ ID NO 22
<211> LENGTH: 17
<212> TYPE: PRT
<213> ORGANISM: Recombinant Human

<400> SEQUENCE: 22

Ser Ser Ser Phe Ser Ser Pro Ser Ser Ala Gly Arg His Val Arg Ser
 1               5                  10                  15

Tyr

<210> SEQ ID NO 23
<211> LENGTH: 18
<212> TYPE: PRT
<213> ORGANISM: Recombinant Human

<400> SEQUENCE: 23

Ser Ser Ser Ser Phe Ser Ser Pro Ser Ser Ala Gly Arg His Val Arg
 1               5                  10                  15

Ser Tyr
```

<210> SEQ ID NO 24
<211> LENGTH: 19
<212> TYPE: PRT
<213> ORGANISM: Recombinant Human

<400> SEQUENCE: 24

Ser Ser Ser Ser Ser Phe Ser Ser Pro Ser Ser Ala Gly Arg His Val
 1               5                  10                  15
Arg Ser Tyr

<210> SEQ ID NO 25
<211> LENGTH: 20
<212> TYPE: PRT
<213> ORGANISM: Recombinant Human

<400> SEQUENCE: 25

Asn Ser Ser Ser Ser Ser Phe Ser Ser Pro Ser Ser Ala Gly Arg His
 1               5                  10                  15
Val Arg Ser Tyr
             20

<210> SEQ ID NO 26
<211> LENGTH: 21
<212> TYPE: PRT
<213> ORGANISM: Recombinant Human

<400> SEQUENCE: 26

Thr Asn Ser Ser Ser Ser Ser Phe Ser Ser Pro Ser Ser Ala Gly Arg
 1               5                  10                  15
His Val Arg Ser Tyr
             20

<210> SEQ ID NO 27
<211> LENGTH: 22
<212> TYPE: PRT
<213> ORGANISM: Recombinant Human

<400> SEQUENCE: 27

Ala Thr Asn Ser Ser Ser Ser Ser Phe Ser Ser Pro Ser Ser Ala Gly
 1               5                  10                  15
Arg His Val Arg Ser Tyr
             20

<210> SEQ ID NO 28
<211> LENGTH: 23
<212> TYPE: PRT
<213> ORGANISM: Recombinant Human

<400> SEQUENCE: 28

Glu Ala Thr Asn Ser Ser Ser Ser Ser Phe Ser Ser Pro Ser Ser Ala
 1               5                  10                  15
Gly Arg His Val Arg Ser Tyr
             20

<210> SEQ ID NO 29
<211> LENGTH: 24
<212> TYPE: PRT
<213> ORGANISM: Recombinant Human

<400> SEQUENCE: 29

Pro Glu Ala Thr Asn Ser Ser Ser Ser Ser Phe Ser Ser Pro Ser Ser
 1               5                  10                  15

Ala Gly Arg His Val Arg Ser Tyr
            20

<210> SEQ ID NO 30
<211> LENGTH: 25
<212> TYPE: PRT
<213> ORGANISM: Recombinant Human

<400> SEQUENCE: 30

Ser Pro Glu Ala Thr Asn Ser Ser Ser Ser Phe Ser Ser Pro Ser
 1               5                  10                  15

Ser Ala Gly Arg His Val Arg Ser Tyr
            20                  25

<210> SEQ ID NO 31
<211> LENGTH: 26
<212> TYPE: PRT
<213> ORGANISM: Recombinant Human

<400> SEQUENCE: 31

Val Ser Pro Glu Ala Thr Asn Ser Ser Ser Ser Phe Ser Ser Pro
 1               5                  10                  15

Ser Ser Ala Gly Arg His Val Arg Ser Tyr
            20                  25

<210> SEQ ID NO 32
<211> LENGTH: 27
<212> TYPE: PRT
<213> ORGANISM: Recombinant Human

<400> SEQUENCE: 32

Met Val Ser Pro Glu Ala Thr Asn Ser Ser Ser Ser Phe Ser Ser
 1               5                  10                  15

Pro Ser Ser Ala Gly Arg His Val Arg Ser Tyr
            20                  25

<210> SEQ ID NO 33
<211> LENGTH: 28
<212> TYPE: PRT
<213> ORGANISM: Recombinant Human

<400> SEQUENCE: 33

Asp Met Val Ser Pro Glu Ala Thr Asn Ser Ser Ser Ser Phe Ser
 1               5                  10                  15

Ser Pro Ser Ser Ala Gly Arg His Val Arg Ser Tyr
            20                  25

<210> SEQ ID NO 34
<211> LENGTH: 29
<212> TYPE: PRT
<213> ORGANISM: Recombinant Human

<400> SEQUENCE: 34

Gln Asp Met Val Ser Pro Glu Ala Thr Asn Ser Ser Ser Ser Phe
 1               5                  10                  15

Ser Ser Pro Ser Ser Ala Gly Arg His Val Arg Ser Tyr
            20                  25

<210> SEQ ID NO 35
<211> LENGTH: 30
<212> TYPE: PRT
<213> ORGANISM: Recombinant Human

```
<400> SEQUENCE: 35

Gly Gln Asp Met Val Ser Pro Glu Ala Thr Asn Ser Ser Ser Ser
  1               5                  10                  15

Phe Ser Ser Pro Ser Ser Ala Gly Arg His Val Arg Ser Tyr
                 20                  25                  30

<210> SEQ ID NO 36
<211> LENGTH: 31
<212> TYPE: PRT
<213> ORGANISM: Recombinant Human

<400> SEQUENCE: 36

Leu Gly Gln Asp Met Val Ser Pro Glu Ala Thr Asn Ser Ser Ser
  1               5                  10                  15

Ser Phe Ser Ser Pro Ser Ser Ala Gly Arg His Val Arg Ser Tyr
                 20                  25                  30

<210> SEQ ID NO 37
<211> LENGTH: 32
<212> TYPE: PRT
<213> ORGANISM: Recombinant Human

<400> SEQUENCE: 37

Ala Leu Gly Gln Asp Met Val Ser Pro Glu Ala Thr Asn Ser Ser
  1               5                  10                  15

Ser Ser Phe Ser Ser Pro Ser Ser Ala Gly Arg His Val Arg Ser Tyr
                 20                  25                  30

<210> SEQ ID NO 38
<211> LENGTH: 33
<212> TYPE: PRT
<213> ORGANISM: Recombinant Human

<400> SEQUENCE: 38

Gln Ala Leu Gly Gln Asp Met Val Ser Pro Glu Ala Thr Asn Ser Ser
  1               5                  10                  15

Ser Ser Ser Phe Ser Ser Pro Ser Ser Ala Gly Arg His Val Arg Ser
                 20                  25                  30

Tyr

<210> SEQ ID NO 39
<211> LENGTH: 34
<212> TYPE: PRT
<213> ORGANISM: Recombinant Human

<400> SEQUENCE: 39

Cys Gln Ala Leu Gly Gln Asp Met Val Ser Pro Glu Ala Thr Asn Ser
  1               5                  10                  15

Ser Ser Ser Ser Phe Ser Ser Pro Ser Ser Ala Gly Arg His Val Arg
                 20                  25                  30

Ser Tyr

<210> SEQ ID NO 40
<211> LENGTH: 4
<212> TYPE: PRT
<213> ORGANISM: Recombinant Human

<400> SEQUENCE: 40

Met Val Val His
  1
```

<210> SEQ ID NO 41
<211> LENGTH: 5
<212> TYPE: PRT
<213> ORGANISM: Recombinant Human

<400> SEQUENCE: 41

Met Val Val His Ser
 1               5

<210> SEQ ID NO 42
<211> LENGTH: 36
<212> TYPE: DNA
<213> ORGANISM: Recombinant Human

<400> SEQUENCE: 42
aaacaacata tggtttctcc ggaggctacc aactcc                        36

<210> SEQ ID NO 43
<211> LENGTH: 35
<212> TYPE: DNA
<213> ORGANISM: Recombinant Human

<400> SEQUENCE: 43
aaacaaggat cctttatgag tggaccacca tgggg                         35

<210> SEQ ID NO 44
<211> LENGTH: 47
<212> TYPE: DNA
<213> ORGANISM: Recombinant Human

<400> SEQUENCE: 44
ctagcgatga cgatgataaa caggctctgg gtcaggacat ggtttct            47

<210> SEQ ID NO 45
<211> LENGTH: 47
<212> TYPE: DNA
<213> ORGANISM: Recombinant Human

<400> SEQUENCE: 45
ccggagaaac catgtcctga cccagagcct gtttatcatc gtcatcg            47

<210> SEQ ID NO 46
<211> LENGTH: 45
<212> TYPE: DNA
<213> ORGANISM: Recombinant Human

<400> SEQUENCE: 46
ggaggaataa catatgtcct acaatcacct gcagggagat gtccg              45

<210> SEQ ID NO 47
<211> LENGTH: 35
<212> TYPE: DNA
<213> ORGANISM: Recombinant Human

<400> SEQUENCE: 47
aaacaaggat cctttatgag tggaccacca tgggg                         35

<210> SEQ ID NO 48
<211> LENGTH: 47
<212> TYPE: DNA
<213> ORGANISM: Recombinant Human

<400> SEQUENCE: 48

```
ttagattcta gatttgtttt aactaattaa aggaggaata acatatg          47
```

<210> SEQ ID NO 49
<211> LENGTH: 35
<212> TYPE: DNA
<213> ORGANISM: Recombinant Human

<400> SEQUENCE: 49

```
aaacaaggat cctttatgag tggaccacca tgggg                        35
```

<210> SEQ ID NO 50
<211> LENGTH: 53
<212> TYPE: DNA
<213> ORGANISM: Recombinant Human

<400> SEQUENCE: 50

```
aaacaacata tgtcttctcc ttcctctgca ggtaggcatg tgcggagcta caa    53
```

<210> SEQ ID NO 51
<211> LENGTH: 35
<212> TYPE: DNA
<213> ORGANISM: Recombinant Human

<400> SEQUENCE: 51

```
aaacaaggat cctttatgag tggaccacca tgggg                        35
```

<210> SEQ ID NO 52
<211> LENGTH: 25
<212> TYPE: DNA
<213> ORGANISM: Recombinant Human

<400> SEQUENCE: 52

```
tatgctgggt caggacatgg tttct                                   25
```

<210> SEQ ID NO 53
<211> LENGTH: 27
<212> TYPE: DNA
<213> ORGANISM: Recombinant Human

<400> SEQUENCE: 53

```
ccggagaaac catgtcctga cccagca                                 27
```

<210> SEQ ID NO 54
<211> LENGTH: 51
<212> TYPE: DNA
<213> ORGANISM: Recombinant Human

<400> SEQUENCE: 54

```
ccggaggcta ccaactctag ctccagcagc ttctcctctc ctagctctgc a      51
```

<210> SEQ ID NO 55
<211> LENGTH: 43
<212> TYPE: DNA
<213> ORGANISM: Recombinant Human

<400> SEQUENCE: 55

```
gagctaggag aggagaagct gctggagcta gagttggtag cct               43
```

<210> SEQ ID NO 56
<211> LENGTH: 25
<212> TYPE: DNA
<213> ORGANISM: Recombinant Human

<400> SEQUENCE: 56

```
aacacctatg catcttttaa ctggc                                    25

<210> SEQ ID NO 57
<211> LENGTH: 29
<212> TYPE: DNA
<213> ORGANISM: Recombinant Human

<400> SEQUENCE: 57
gtccctgcct gggagctcct tttccattc                                29

<210> SEQ ID NO 58
<211> LENGTH: 30
<212> TYPE: DNA
<213> ORGANISM: Recombinant Human

<400> SEQUENCE: 58
gctcccaggc agggacaaaa aacaagaagg                               30

<210> SEQ ID NO 59
<211> LENGTH: 29
<212> TYPE: DNA
<213> ORGANISM: Recombinant Human

<400> SEQUENCE: 59
aacaaaggat cctttatgag tggaccacc                                29

<210> SEQ ID NO 60
<211> LENGTH: 25
<212> TYPE: DNA
<213> ORGANISM: Recombinant Human

<400> SEQUENCE: 60
aacacctatg catcttttaa ctggc                                    25

<210> SEQ ID NO 61
<211> LENGTH: 29
<212> TYPE: DNA
<213> ORGANISM: Recombinant Human

<400> SEQUENCE: 61
aacaaaggat cctttatgag tggaccacc                                29

<210> SEQ ID NO 62
<211> LENGTH: 29
<212> TYPE: DNA
<213> ORGANISM: Recombinant Human

<400> SEQUENCE: 62
aacaaaggat cctttatgag tggaccacc                                29

<210> SEQ ID NO 63
<211> LENGTH: 51
<212> TYPE: DNA
<213> ORGANISM: Recombinant Human

<400> SEQUENCE: 63
ccggaggcta ccaactctag ctccagcagc ttctcctctc ctagctctgc a        51
```